United States Patent
Wood et al.

(10) Patent No.: US 10,691,773 B2
(45) Date of Patent: Jun. 23, 2020

(54) CELL PROCESSING TECHNIQUES

(71) Applicant: General Electric Company, Schenectady, NY (US)

(72) Inventors: Nichole Lea Wood, Niskayuna, NY (US); Lynn Ann DeRose, Gloversville, NY (US); Kunter Seref Akbay, Niskayuna, NY (US); Christopher Donald Johnson, Clifton Park, NY (US); Reginald Donovan Smith, Schenectady, NY (US); Dolores Baksh, North Easton, MA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 223 days.

(21) Appl. No.: 14/984,766

(22) Filed: Dec. 30, 2015

(65) Prior Publication Data
US 2017/0193168 A1    Jul. 6, 2017

(51) Int. Cl.
| | |
|---|---|
| G16H 70/20 | (2018.01) |
| G16H 10/60 | (2018.01) |
| A61K 35/17 | (2015.01) |
| G16H 50/20 | (2018.01) |
| G06F 19/00 | (2018.01) |
| G01N 33/15 | (2006.01) |

(52) U.S. Cl.
CPC ............ *G06F 19/325* (2013.01); *A61K 35/17* (2013.01); *G01N 33/15* (2013.01); *G16H 10/60* (2018.01); *G16H 50/20* (2018.01)

(58) Field of Classification Search
CPC ... G06F 19/325; C12N 2511/00; A61K 35/17; G16H 10/40; G16H 10/50
USPC ............................................. 705/3, 2
See application file for complete search history.

(56) References Cited

U.S. PATENT DOCUMENTS

| | | |
|---|---|---|
| 5,837,249 A | 11/1998 | Herber-Katz |
| 8,027,849 B2 | 9/2011 | Johnson et al. |
| 8,311,850 B2 | 11/2012 | Johnson et al. |
| 2002/0001841 A1 | 1/2002 | Kaltoft et al. |
| 2002/0155487 A1 | 10/2002 | Greenberger et al. |

(Continued)

FOREIGN PATENT DOCUMENTS

WO    2014186469 A2    11/2014

OTHER PUBLICATIONS

Qui, R.G., "RFID-enabled automation in support of factory integration," Robotics and Computer-Integrated Manufacturing, vol. 23, Issue 6, pp. 677-683 (Dec. 2007).

(Continued)

*Primary Examiner* — Hiep V Nguyen
(74) *Attorney, Agent, or Firm* — Eversheds Sutherland (US) LLP

(57) ABSTRACT

The present disclosure relates to cell processing techniques. By way of example, a cell processing system may include a plurality of sample processing devices configured to process patient samples and a plurality of readers respectively associated with the plurality of sample processing devices, wherein each reader is configured to read information from tracking devices associated with respective patient samples. The system may also include a controller that uses information from the readers to provide an estimated completion time for a patient sample based on availability of the sample processing devices.

15 Claims, 14 Drawing Sheets

(56) References Cited

U.S. PATENT DOCUMENTS

| | | |
|---|---|---|
| 2004/0054142 A1 | 3/2004 | Cassart et al. |
| 2005/0158397 A1 | 7/2005 | Choppe et al. |
| 2009/0119126 A1 | 5/2009 | Johnson et al. |
| 2012/0029832 A1* | 2/2012 | Dodgson ............ B01L 3/50825 702/19 |
| 2014/0212398 A1 | 7/2014 | Reisner et al. |
| 2014/0227237 A1* | 8/2014 | June ...................... C07K 14/82 424/93.21 |
| 2017/0161466 A1 | 6/2017 | Amaratunga et al. |
| 2017/0193167 A1 | 7/2017 | Wood et al. |
| 2017/0199211 A1 | 7/2017 | Ghouze et al. |
| 2018/0005156 A1 | 1/2018 | Baksh et al. |

OTHER PUBLICATIONS

International Search Report and Written Opinion issued in connection with corresponding PCT Application No. PCT/EP2016/082108 dated Apr. 13, 2017.

Sharpe et al., Genetically modified T cells in cancer therapy: opportunities and challenges, DMM Disease Models and Mechanisms, vol. 8, Issue 4, pp. 337-350, Apr. 2015.

Wiraja et al., Aptamer technology for tracking cells' status & function, Molecular and cellular Therapies, vol. 2, Issue 33, 2014, 22 pages.

GE Xuri™. Believe in better futures. Finding solutions. Advancing breakthrough cell therapies, Apr. 2014, pp. 1-20.

* cited by examiner

FIG. 14

CELL PROCESSING TECHNIQUES

BACKGROUND

The subject matter disclosed herein relates to cell therapy techniques for optimally processing and delivering cells to a therapy patient.

In cellular immunotherapies, a patient's own blood, fluid, tissue, or cell sample is typically collected in a hospital/clinical setting and transferred to a central location for manufacturing of a cellular therapy generated from and/or based on the collected sample. The cellular therapy product is then delivered back to a clinical setting for infusion into same patient for autologous therapy or a different patient for non-autologous therapy. Production of the cell therapy product may take several days, utilizing a dynamic plurality of resources to achieve optimal assignment for one or more samples according to their specific biological response rates and particular steps may have variable or unpredictable output times depending on the quality of the initial sample. Accordingly, because processing time for each sample is highly variable to achieve a specified therapeutic quality such as cell state and count, scheduling patients and care delivery resources for return visits to administer the manufactured cell therapy product is dynamically controlled to achieve the specified cell quantity and quality.

BRIEF DESCRIPTION

In one embodiment, a cell therapy manufacturing system is provided. The system includes a sample container configured to hold a cell therapy sample and a reader co-located with a sample processing device or a manufacturing location and configured to receive an identification signal from a tracking device coupled to the sample container. The system also includes a controller operatively coupled to the reader and configured to access a sample processing timeline of a processing protocol associated with the identification signal upon receipt of the identification signal; determine if variations from the processing protocol have occurred that alter the sample processing timeline based at least in part on a time of receipt of the identification signal; provide one or more updated estimated completion times of the processing protocol; and communicate the updated estimated completion time of the sample processing timeline.

In another embodiment, a system is provided. The system includes a plurality of sample processing devices configured to process patient samples. The system also includes a plurality of readers respectively associated with the plurality of sample processing devices, wherein each reader is configured to read information from tracking devices associated with respective patient samples. The system also includes a controller comprising a processor configured to: receive a request to process a new patient sample according to a processing protocol; determine availability for the plurality of sample processing devices based on signals from the plurality of readers; and provide an estimated completion time for the processing protocol based at least in part on the availability. For example, in one embodiment, the system may take into account a clinical priority of a sample when assigning resources. In another embodiment, the system may take into account the availability or states of various resources (e.g., whether maintenance or downtime is scheduled). The system may also provide a rank ordered sequence of activities to optimally achieve throughput and meet turnaround time while maintaining cell quality.

In another embodiment, a cell processing method is provided. The method includes the steps of receiving at a processing facility a patient sample from a collection facility; tracking the patient sample within the processing facility using one or more tracking devices coupled to one or more sample processing containers; processing the patient sample to generate a processed patient sample using a plurality of sample processing devices; capturing the identification information from the plurality of sample processing containers using a plurality of readers associated with respective sample processing devices; receiving data related to the patient sample from one or more sample processing devices; estimating a completion time for the patient sample based on the data and the identification information; and providing the completion time to a remote facility.

In another embodiment, a cell processing tracking device is provided. The device includes a sample processing container configured to contain a volume of a patient sample; a sealable receptacle incorporated into or coupled to the sample processing container; and a tracking device encapsulated by a fluid-resistant film and disposed in the sealable receptacle and wherein the tracking device encapsulated by a fluid-resistant film is configured to be removed from the sealable receptacle by an operator to be sterilized and reused, wherein the tracking device stores identification information for the patient sample that is erased or overwritten when the tracking device is reused.

In another embodiment, a system is provided. The system includes a controller comprising a processor configured to: receive information about a patient with a clinical diagnosis; generate a request to process a sample of the patient according to a processing protocol; receive status information comprising available times for sample processing according to the processing protocol from a cell processing facility; receive information related to an availability of one or more resources; and determine a sample acquisition time range that permits transport of the sample to the sample processing facility within a predetermined window from one of the available times that is coincident with the availability of the one or more resources.

In another embodiment, a system is provided. The system includes a controller comprising a processor configured to: receive information about a patient with a clinical diagnosis; generate a request to process a sample of the patient according to a processing protocol; receive status information comprising a time for completion of sample processing according to the processing protocol from a cell processing facility; receive information related to an availability of one or more resources; and determine a therapy administration time range that permits transport of the sample to a therapy administration facility within a predetermined window of the estimated completion time that is coincident with the availability of the one or more resources.

In another embodiment, a system is provided. The system includes a plurality of sample processing devices configured to process patient samples; a plurality of readers respectively associated with the plurality of sample processing devices, wherein each reader is configured to read information from tracking devices associated with respective patient samples; and a controller comprising a processor configured to: receive a request to process a new patient sample according to a processing protocol; estimate a presence of a potential bottleneck in the manufacturing workflow based on an availability of one or more of the plurality of sample processing devices based on signals from the plurality of readers; and update the number of sample processing devices at each step to avoid the bottleneck In another embodiment, a system is provided. The system includes a plurality of sample processing devices configured to process patient samples; a plurality of readers respectively associated with the plurality of sample processing devices, wherein each reader is configured to read information from tracking devices associated with respective patient samples; and a controller configured to: receive a request to process a new patient sample according to a processing protocol; receive a cell count data from the processing device while the patient sample is being processed; estimate the completion time based on cell count data and availability of a next sample processing device in the sample processing workflow.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 14 is an example of a user interface for tracking patient sample in a cell therapy process according to an embodiment of the present disclosure.

DETAILED DESCRIPTION

Figure 1:
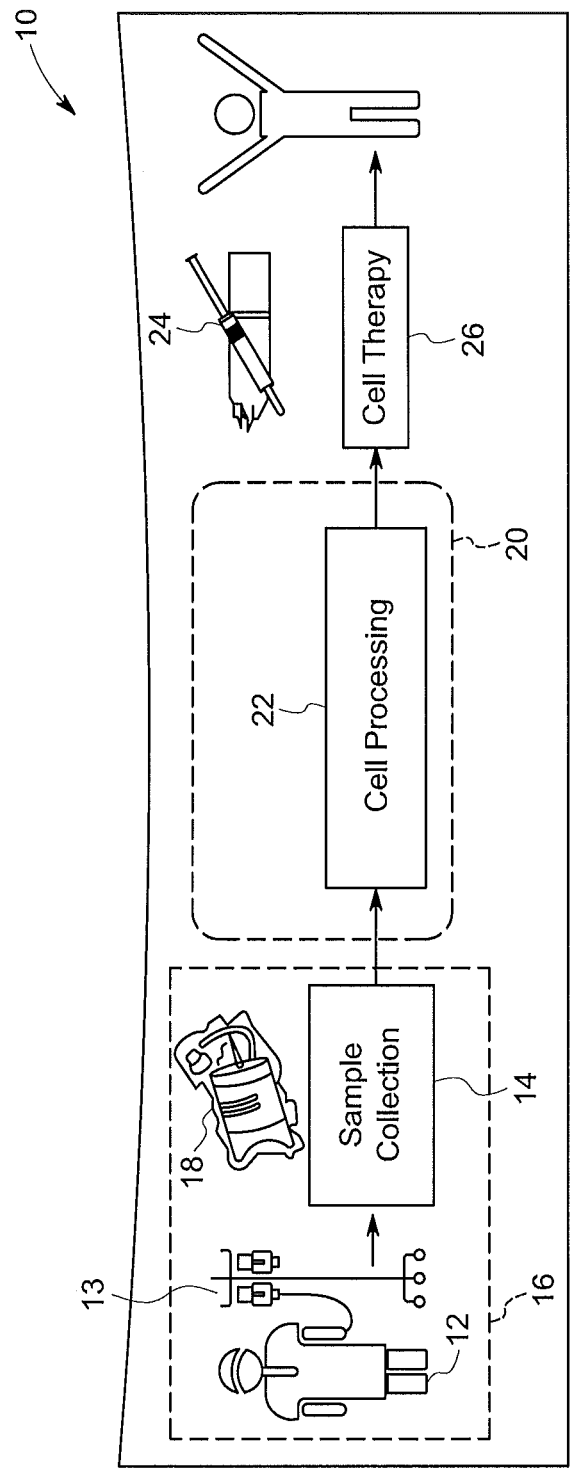
FIG. 1 is a schematic representation of a cell therapy treatment according to an embodiment of the present disclosure.

The disclosed embodiments may be used to facilitate production of a cellular therapeutic in order to achieve a specified cell count or quality while minimizing turnaround time for the "vein-to-vein" workflow including patient sample collection, cell therapy manufacturing, and delivery back to the patient. Each patient sample may be subject to variability due to the unique biological characteristics of the individual patient samples and variations in biological processes during the manufacturing phase. For example, the initial patient starting material, often an apheresis blood product, will vary in the quantity of target cells (e.g. T-cells) for use in autologous cell therapies. In addition, the growth rate and differentiation may vary from one donor sample to the next during the manufacturing process despite use of a standardized protocol. Standard operating protocols (SOPs) are developed in manufacturing processes to minimize variation. However these SOPs often do not address all of the variability that can occur. For example, if cells are growing slower than expected, as measured by a cell count assay, the SOP may need to be modified in real-time in order to extend the duration of the cell expansion phase until the target cell quantity is achieved. Such variability, if not addressed, can result in a lower quality cell product or at worst, loss of a patient sample. For that reason detecting process variability in real time and providing automated control or directed I/O to operators with specific, identified and ranked opportunities to modify the protocol as needed and ensure a successful manufacturing run, enables cell quality metrics to be achieved.

Biological variability can also dynamically change the demand for labor and equipment resources in the facility during the manufacturing process. Some process steps require certain resources for short periods of time while others can require multiple contiguous days of a resource (e.g. incubator space, bioreactor). Not having the right resources when needed may impact the cell quality and will lengthen the overall turnaround time. In addition, this variability can affect the manufacturer's ability to receive additional patient samples for processing and/or accurately schedule cell product delivery to the clinical setting for therapeutic administration, or to differentially expedite a therapy through the process for a prioritized order.

Provided herein are techniques to minimize overall time to manufacture while improving autologous cell therapy product yield and quality that, in turn, may increase the effectiveness of an autologous cell therapy manufacturing process for one or multiple patients of homogenous or stratified clinical priorities. The techniques allocate production resources as a function of patient attributes (such as comparative degree of urgency), the expansion rate of one or more patient cell samples at a given process step, and the sequencing of sample attainment, processing and delivery. In certain embodiments, samples are scheduled for production as a function of available cell expansion production capacity and required clinical outcomes in the care plan. In another embodiment, samples are scheduled for production as a function of the biological process configuration to achieve a specified sample demand function at a specified service level that is optionally offered as a performance based service where cell count and/or turnaround time and/or cost is commercially warranted. In another embodiment, the techniques permit dynamic process control to achieve cell rate, count and quality objectives. In yet another embodiment, the techniques assure tracking and safety of cell samples from vein to vein when the sample is contiguous or, optionally, divided. Sample delivery back to the patient is set by the rate and quality of the cell production and availability of clinical delivery resources. The disclosed embodiments permit allocation of production resources as a function of patient attributes (such as comparative degree of urgency or other metric of importance as may be devised), the expansion rate of one or more patient cell samples at a given process step, and the logistical sequencing of sample attainment, processing and delivery.

While certain embodiments of the disclosure are directed towards autologous cell therapies that involve collection, manipulation, and re-insertion of a patient's own cells, the applications of the disclosed techniques may include other patient specific cellular therapies (one patient donor provides cells for single but different patient recipient), or allogenic cells, modified human cells, or xenotransplantation of non-human cells. Cell based therapies that are contemplated as being used in conjunction with the disclosed techniques may include therapies for organ or tissue regeneration, cancer treatment, blood disorders, immunotherapies, heart disease, or any other cell-based therapies.

FIG. 1 is a schematic representation of an autologous vein-to-vein cell therapy technique 10. A patient 12 in need of cell therapy treatment is scheduled for sample collection 14 at a collection facility 16, typically a hospital or outpatient treatment facility. The collected sample 18, which may be a blood, tissue, or other cell sample, is then provided to a cell therapy processing facility 20, where the collected sample 18 undergoes appropriate processing via a cell processing protocol 22 to generate a cell therapy product 24. However, in certain embodiments, the collected sample 18 is processed at a point-of-care facility co-located with the collection facility 16. The manufactured cell therapy product 24 is then used in a cell therapy treatment 26 for the patient 12. For example, the cell therapy product may be injected into the patient's vein. Before the cell therapy product 24 is provided for cell therapy treatment 26, the cell therapy product 24 may be assessed for adherence to regulatory (e.g., FDA) quality and safety requirements. For example, such requirements may include sterility, a particular cell count, or a particular count of viable cells, e.g., a minimum cell viability of 70%. The patient may have other clinical activity 13, such as chemotherapy which is also co-managed with cell therapy.

Figure 2:
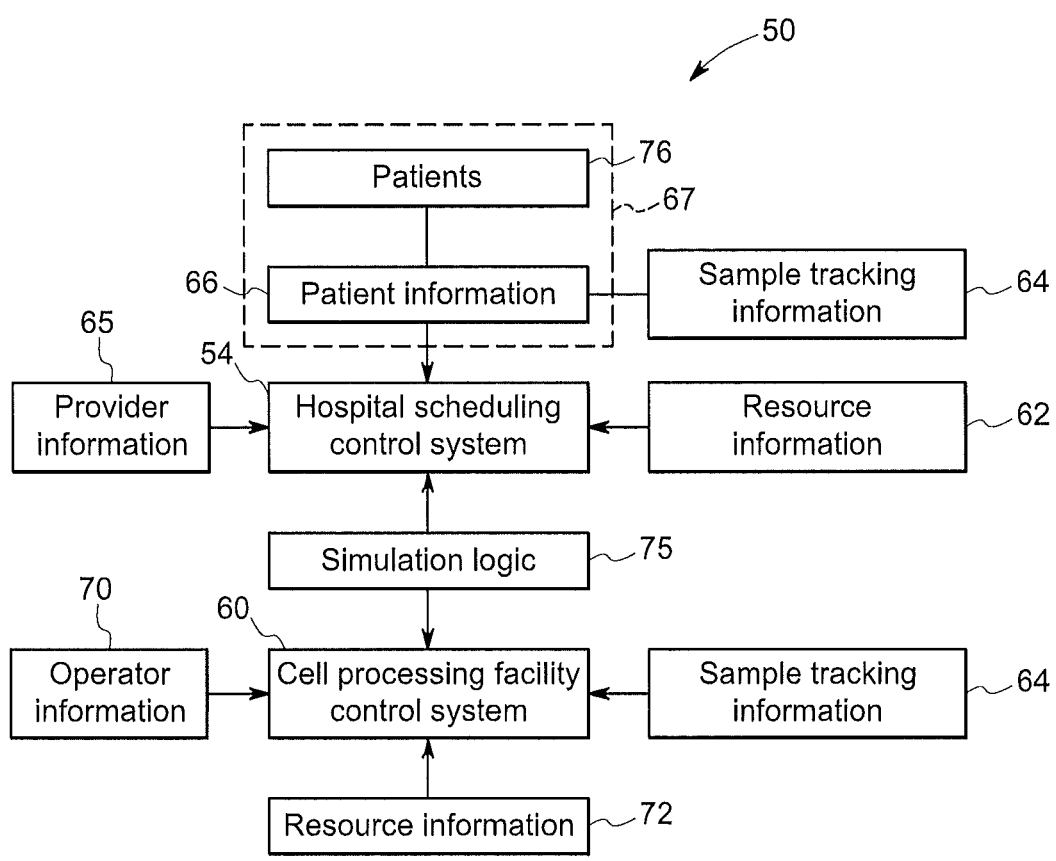
FIG. 2 is a schematic representation of an interaction between a hospital scheduling system and a cell processing facility control system.

FIG. 2 is a block diagram of a system 50 for tracking cell therapy production from vein-to-vein. While the system 50 is shown with a hospital scheduling controller 54 associated with a hospital or other medical facility and that is configured to at least in part access a remote cell processing facility controller 60, certain functions of these separate components may be combined. That is, the system 50, including the controller 60 and the controller 54, may be combined into a single control system. Alternatively, certain functions of the controllers 54, 60 may be distributed in a cloud computing environment. Accordingly, certain functions of the controllers 54, 60 of the system 50 may be combined or exchanged as appropriate. Further, it should be understood that the hospital scheduling controller 54 may access and communicate with multiple cell processing facility control systems 60. In addition, each cell processing facility controller 60 may receive samples from multiple hospitals, each with a dedicated scheduling controller 54. The system 50 may use various inputs and rules-based logic to schedule patients for patient sample acquisition (e.g., blood draws), and to schedule transportation of patient samples to the cell processing facility, specify a production plan and optionally provide an acuity and/or turnaround time request for a cell therapy product based on the patient sample, determine a cell processing workflow, dynamically estimate or model a completion time for production of the cell therapy product, and specifically schedule the care providers and physical assets to administer the cell therapy product to the patient.

Hospital resource information 62 (e.g., room availability), sample tracking information 64, care provider information 65, and patient information 66 in the system 50 may be used as inputs to design the flow sequence, sizing, control and transport rules for each patient sample. The cell processing facility controller 60 may also track production of each patient sample using operator information 70, sample tracking information 64, and resource information 72 to determine the vein to vein process capacities and movement rules such that the key process indicators such as service level at a given (or testing a hypothetical) patient demand or turnaround time are met. In one embodiment, the system 50 includes simulation logic 75, such as a simulation-based transfer function, such as for example, a discrete event simulation, that is used as the controlling logic of the system 50 to orchestrate the cell expansion demand arrival pattern, allocate production machine assignments, forecast machine durations based upon the dynamical expansion rate of cells in the tracked process, change flow patterns within production as a function of optimal machine assignment and machine availability or reliability or comparative effectiveness on a given cell sample, forecast completion time for patient therapy delivery and orchestration of the delivering clinic so that logistically, the expanded cells are shipped, transported to and administered to the patient with minimal loss of cell count and quality due to delays. The system 50 facilitates improved control of cell quality for one or a portfolio of changing patient samples. The simulation logic 75 may be part of one or both of the hospital scheduling controller 54 or the cell processing facility controller 60.

In one embodiment, a patient diagnosed with cancer and deemed to be a candidate for the cell therapy according to the disclosed techniques is introduced to the system by a care provider. As noted, the care provider information 65 may be used as an input to the system 50. A measure of clinical urgency is ascribed as an attribute of the patient 76 along with other attributes such as name, biological and medical states, insurance, and desired logistical dates as part of the patient information 66. The system acquires or accesses the physical states of the resource information 62, such as the production assets, personnel, consumables and the equipment or space to physically attain samples and return the processed batch. The system 50 may create a blank new patient object 67 and write the preferences and indicators into the structured taxonomy of the patient state object. The patient object is a collection of state engines and descriptors as well as a basic autonomous agent in the simulation which is given a care plan by the system simulator and optimizer. This autonomous agent logic is continuously updated by the master control so that, should the control system fail or be corrupted, the patient object will have the most current schedule and assignment information such as what the optimized sample processing sequences are. These sequences include a deterministic "best assignment" (of resources and times) and viable and ranked alternatives. In addition to being written into the patient object, a mirror is written into the systems data archive concurrently by the system simulation logic 75. The simulation logic 75 is calculated and updated to expect the patient arrival and processing at given times for each process step. The object of this feature is to ensure that there is synchronization between the control, patient object and its autonomous twin which is placed with the sample, historical data and the local machine control. Should any communication failure occur and if a cell sequencing step is attempted that varies from the processing protocol, the local machine control logic and the system itself will logically respond and alert a process warning.

The simulation logic 75 designs the tasks, resources and operational policies related to the core temporal flow of the system by creating entities and resources that will be logically controlled by the transition (workflow) logic, which is also the operational decision support policies that effect the control of the system when the simulator is transitioned from its design to operational modes.

For example, individual patients 76 with patient information 66 are entities in the simulation logic. The system models and tracks one specific and unique patient 76 or several patients 76 that may each be unique from each other or may be a subset of all patients but with attributes that make them a group of patients that are of special interest. An example of being of special interest is a demographic descriptor (e.g. females between 60-65 years with a certain diagnosis, patients of "Dr. x", patients who are selected to use cell production process or facility "y", or any other meaningful descriptor that makes a subset or all patients a member of a stratified or labeled or controlled group). Patients 76 may be made to be representatives of groups, for example the patient 76 is a patient type who represents other patients of like type. Patient demand into the system is modeled as an arrival pattern where specific patients 76 with their unique attributes are presented as arriving at a point in time or may be a sequence of patients or patient types arriving through time. Patients are characterized by demographical and clinical attributes, which may be used as inputs to the simulation logic 75.

In operation, hypothetical duration estimations and resource availabilities are replaced with the actual state information provided via various tracking interfaces, user inputs, sensors, etc., in real time at steps where actual physical movement of the samples and processing is occurring, and in historical aggregation. For example, tracking devices physically coupled to the patient sample may provide wireless signals that are used to track the patient sample within a cell processing facility as provided herein. Such information may be provided to the system 50 as an input.

The real time state information of the workflow is compared with the original schedule and the dynamical forecast of the states in the simulation logic 75. A forecast error from actual states in the present and a likely error from the forecasted states are calculated. The optimization algorithm adjusts the assignment of resources to most optimally meet the schedule and priorities of one or more samples and, if not possible to meet a current patient's schedule and the concurrent need of all other patients.

The control of cell expansion process timing with other clinical activities such as chemotherapy 13 may achieve a clinical outcome resulting from a high cell count of a cell therapy product and minimal delay vein to vein. For example, a patient's in vitro blood cell counts are typically being managed via the administration of chemotherapy and the re-insertion of expanded cells is ideally timed for a given level of blood cell count and condition. The present techniques synchronize these two activities (chemotherapy 13 and manufacturing or processing 22) to minimize degradation or mistiming from the cell expansion process with respect to the biological state the patient's doctor is managing.

In one embodiment, the patient sample is acquired at a hospital, and the hospital scheduling controller 54 forecast the patient into the cell processing facility controller 60 to schedule the future patient sample into the flow of the manufacturing process or processing 22 (FIG. 1) such that capacity is reserved a priori to that patient's sample arriving at the processing facility. Processing is dynamically controlled as a function of a particular patient's cells responding to the expansion process so as to efficiently produce the requisite cell count and quality with respect to all other patient cells also being processed.

Similarly, upon the cell processing system's characterization of cell expansion rate and machine assignments once processing begins, forecasts are made for the cellular therapeutic's reinfusion back into the patient, which the hospital in the example embodiment is then able to consume into its scheduling controller 54 for the purposes of patient scheduling other clinical activity 13 and resource assignment. The present system 50 may also provide the scheduling for patients and resources in place of a hospital's scheduler 54 when said hospital scheduler is not capable of probabilistic forecasting or dynamic workflows. An example embodiment of such a circumstance would be the present system's publishing and consumption of information via a web portal and dynamic data exchange which patients and care providers may log into or receive alerts from.

In certain embodiments, the system 50 forecasts a range of likely future realizations and, as time progresses and potential future realizations reduce into actual measurable actions, the forecast interval is narrowed and the asset assignment, machine and operational logistical control approach a deterministic state. The disclosed system 50 concurrently manages one or many patients whose clinical care is at different stages. For example, a patient 76 may be introduced into the system 50, for example, with no schedule and just, for example, an indicator of clinical urgency, proceeded through scheduling that was then optimized for example current time minus two weeks. The patient's expected sample arrival may be estimated at the current time minus seven to thirteen days characterized by a Poisson distribution with a mode at eleven days, e.g., by the simulation logic 75. As time and events realize in the physical world, scenarios converge and potential resource assignment choices are pruned down.

The present techniques may assess key performance indicators (KPIs) or protocol set points that are dynamically optimized: safety (e.g., right sample on right machine); throughput (e.g., maximization of the number of patients served or cell quality over a specified interval); inventory of work in process (cell batches) minimized; operating expenses related to energy, consumables and labor minimized; fulfillment error (schedule variations from targeted ship date) minimized; maximization of clinical measures for a patient, a stratification of patients or total number of patients. The simulation logic may calculate or model inventory, operating expense, fulfillment, risk and return and clinical measure for a given time period or for a given sample. The processing protocol may be designed with the above set points in mind or as constraints to the logic and any dynamic changes may be made to adhere to the set points.

In one embodiment, the system may calculate one or more metrics for achieving key performance indicators at minimal individual or combined variance or combined weighted variance such that a solution is robust to the variations of exogenous forces such as new patient arrivals, cell production rate, and machine reliability. For example, for each assignment of sample to machine and patient schedule duration that is a selectable choice in the simulation logic, a scenario is produced. Each scenario of assignment to resource is replicated for example, thirty times to capture the effects of variations, such as from the probabilistic assumptions. Variation from plan, objective or just natural variation is calculated for each scenario. The totality of the metric calculation and their variation for each scenario is compared pairwise. For metrics seeking to maximize, the point which is the highest key performance indicator) (KPI) outcome at lowest variation is both optimal and robust. For a metric whose value is desired to be minimized, optimality is lowest value with minimal variation. The simulation and optimization explores the patient logistical scheduling choices, machine assignment choices and responses to rates of change of cell growth, production machine maintenance, shift scheduling and other dynamical choices in the system.

In one embodiment, the present techniques facilitate machine sequencing of sample processing devices to one or more patient samples. The machines may be in parallel or in series. The system 50 assigns a patient sample to one or more sample processing devices by testing the candidate assignments of the one or more patients, through one or more time intervals to find a robust and optimal solution. The optimization is replicated on a continuous basis so that, as any state of device, sample cell growth or patient state changes, a dynamical response is optimized automatically. Accordingly, the system 50 may use empirical, hypothetical, and/or real-time information in building a model to estimate completion time of a cell therapy product for any given patient sample.

Figure 3:
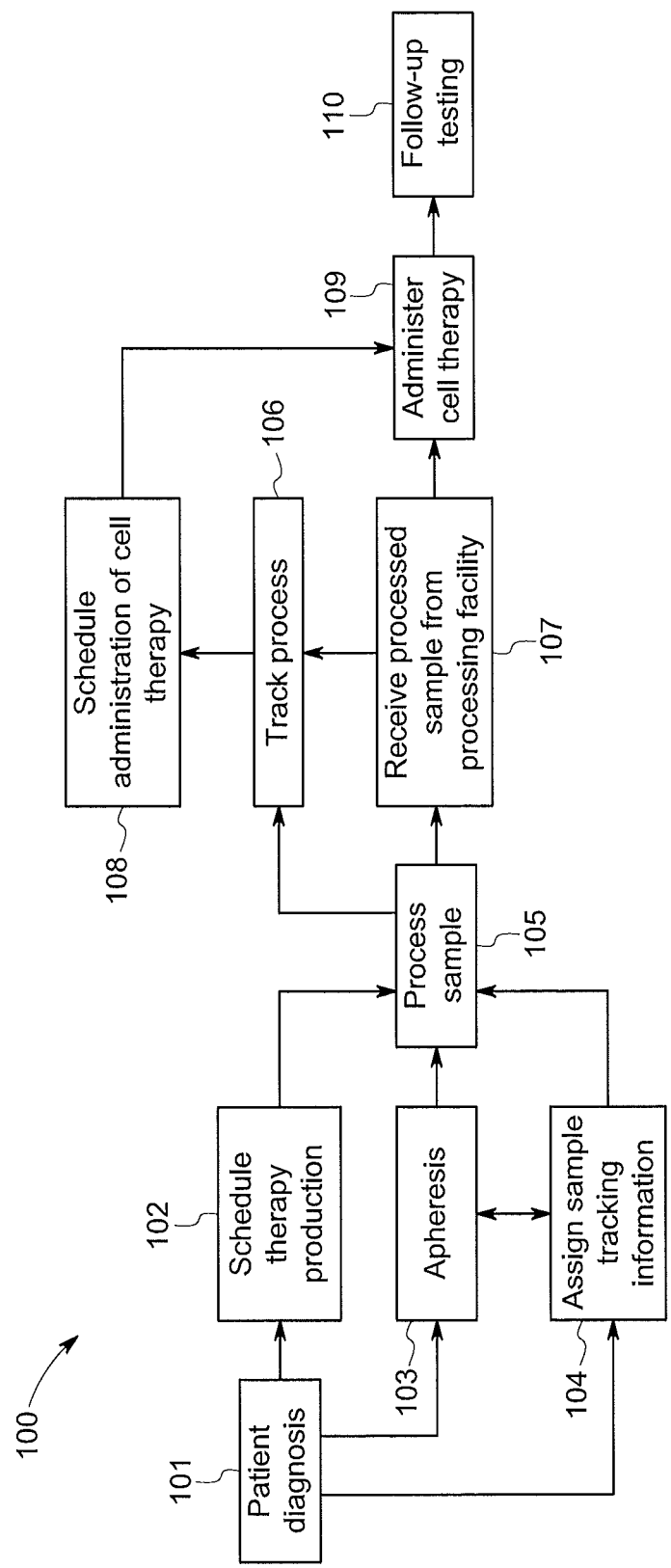
FIG. 3 is a schematic representation of vein to vein therapy process tracking.

FIG. 3 is a schematic representation of an example workflow 100 that may be used in conjunction with the disclosed techniques, e.g., with the system 50 (see FIG. 2). While the depicted workflow 100 includes specific steps that are performed in conjunction with specific system components that are used to process and/or schedule a patient sample, it should be understood that the depicted workflow 100 is an example, and the disclosed techniques may be used in conjunction with other workflows. The workflow 100 may be implemented using a sequential framework to describe the cell and physical system state control. In certain embodiments, the workflow 100 begins with a diagnosis that a patient has cancer 101 and completes when cell therapy delivery has resulted in a final clinical determination of the processes effectiveness.

A patient is determined to have cancer with a clinical diagnosis 101 and is referred to one or more diagnostic tests that calculate the appropriateness measures for cell therapy and the general clinical workflow and timing for the administration of cell therapy, such as the cell count, timeline and resources involved in scheduling a cell therapy production 102. The scheduling may be performed by one or more controllers (e.g., controller 54, controller 60) of the system 50, which manage hospital and/or processing facility schedules and resources. As discussed, the functions of these controllers are part of the system 50. The scheduling of cell therapy production 102 may also involve establishing or selecting a processing protocol or production plan for the patient sample that is designed with the patient's clinical requirements accounted for.

A patient's scheduled blood sample 103 is drawn and assigned tracking information 104 and sent to a facility that is qualified to perform the cell expansion production process where the sample is processed in a facility to manufacture a cell therapy. For example, the cells are expanded and processed using the plurality of resources in the production process 105, which have been designed to optimally achieve a specified service level and are controlled to achieve a cell count and quality as specified by the production plan. Upon expanding the cells and observing the biological production rate the workflow 100 tracks the process 106 and in consideration of the care plan, production continues until a clinical re-infusion is scheduled at a scheduling step 108 by the system. Samples are sent from the lab in a logistical flow to be received 107 for administering patient therapy 109. The effectiveness of the clinical cell therapy treatment is evaluated, e.g., via follow-up testing 110 and, for example, adjusted for being a completed process. In one embodiment, the workflow 100 may be repeated based on the evaluation.

In certain embodiments, the system 50 (see FIG. 2) is able to assess whether a given patient has a type of cancer that would be logistically treatable by the present cell therapy system's capacity. To make the feasibility determination, resources may be assigned that may include space, assets, data and expertise to make the assessment. For example, one such resource is a certain doctor who must be available concurrent with other requisite resources such as, for example, an examination room, apparatus, patient and certain information. These interdependencies are the example logical code in the diagnostic and therapy scheduling entity—where each requisite resource is present at an interval of time before the clinical activity begins, remains present for the anticipated duration of the clinical activity and then are released for other activities. The system 50 calculates the availability of resources over a time horizon using methods as disclosed by Johnson in U.S. Pat. Nos. 8,027,849, 8,311,850, 20090119126 and 20120010901, which are incorporated by reference in their entirety herein for all purposes, which the simulation logic calls as an object with an application protocol interface or as a service, as may be the preference of the user. Similarly, the blood sample acquisition step 103 activates the set of tasks to schedule the clinical services and patient to extract blood for cell amplification purposes. In one embodiment, the system also communicates a clinical sample acquisition time target to align the acquisition of the sample with the specific production capacity such that the system is controlling to achieve cell quality. Delays from sample acquisition to cell expansion can degrade cell count, particularly if cells are processed without freezing.

Figure 4:
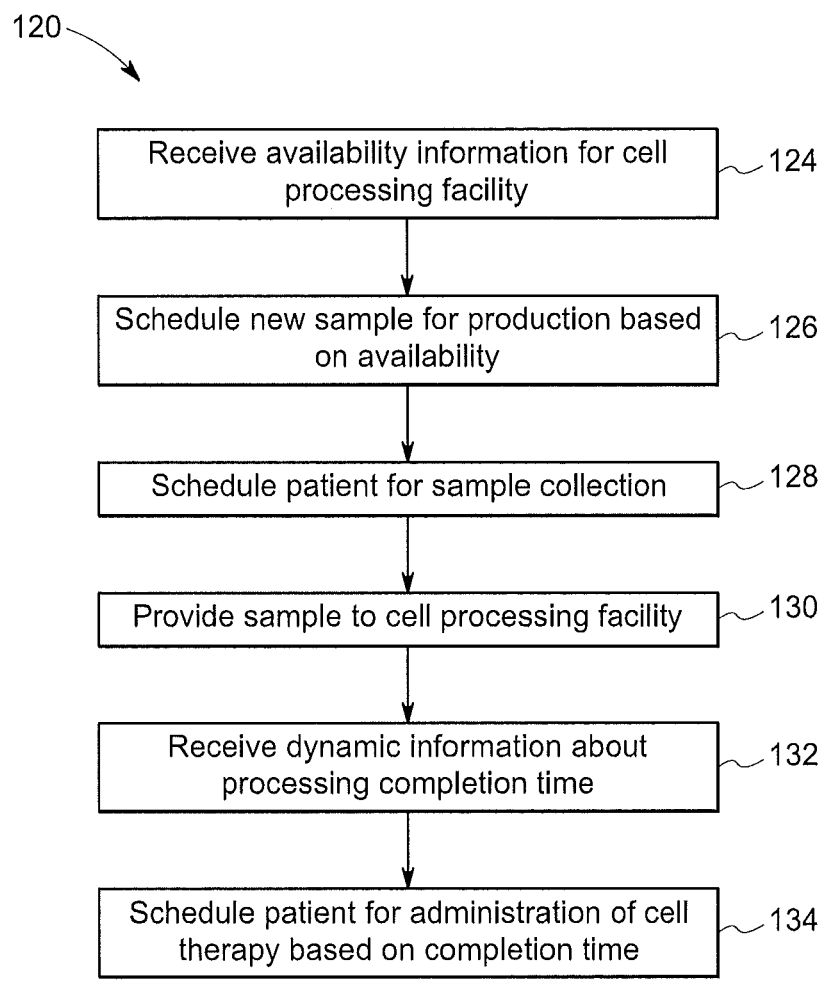
FIG. 4 is a flow diagram of a patient sample scheduling workflow according to an embodiment of the present disclosure.

FIG. 4 is a flow diagram 120 of a vein-to-vein patient sample scheduling workflow in which the system (e.g., system 50) may also assess what the capacities are for each of the production components and their temporal relation to each other with respect to throughput of cell samples being amplified. The capacity and time availability is thus made available to assign a given sample into production at a designated point in time. The sample extraction and transport are timed to have the sample arrive at the production line in the future, into a time period which the production apparatus are prepared to receive it.

In addition, the expanded cell production result is used to administer the cell therapy back to the patient. The simulation (e.g., generated via simulation logic 75, see FIG. 2) initially uses a forecasted probabilistic duration for the expansion to arrive at the targeted cell count, based upon descriptive attributes of the cell biology and the actual production status of the lab with respect to its capacity utilization for the current sample and all other samples being processed and scheduled to be processed. As the actual rate of expansion is observed, the proforma assumptions used in the simulator are updated with actual cell count and quality state information. The simulation, with the benefit of actual changes in cell expansion rate from the current sample and all others, forecasts an estimated processing completion time when the sample will be ready for administration back to the patient, and this forecast or model is provided along with an assessment of availability to take new samples to the system at step 124. The administrative control of the clinic, which schedules the patient, clinical facilities and resources, schedules the sample for production based on the availability (step 126), such as a first available intake date, in the facility and schedules sample acquisition (step 128) and transport to the facility (step 130) based on the forecast or model for production, e.g., the scheduling may be based on a production date where there is minimal time lost from the production expansion completion to cell insertion. The simulation logic accounts for the logical protocols, asset assignment rules, movement policy, movement activity and interdependencies of the requisite resources.

In simulation mode, the durations of tasks, availability of resources, demand scenarios, movement response and assignment logic is assumed based upon prior observation and the control logic engineered into the system. The key process indicators of sample throughput, turnaround time, asset utilization and cell quantity and quality are estimated with the simulation algorithm.

Once the patient sample has reached the cell processing facility, the estimate of the processing completion time is dynamically updated (step 132) based on any changes in the state of the facility and/or the sample itself. For example, cell expansion duration may vary. Additional variability may be introduced in the cell acquisition, expansion and delivery so as to produce a designated number of cells and have them delivered, with minimal loss, for reinsertion into the patient. A third interval is the vein to vein duration.

Tasks and resource consumption are optimally controlled with a constraints-based optimization construct whose task durations are probabilistic and interdependent upon the physical resource limits and electro-mechanical-biological system's state. The task duration forecasts are produced by the discrete event simulation which calculates scenarios in advance of the actual activity. The constraints based method derives critical path for each assignment of resources and patients. Replications are made to characterize variations which result from forecast error, exogenous factors (such as, for example, sample growth rates, machine reliability and operator proficiency). Should the duration at any of the three specified intervals exceed the amount of time desired to achieve a given cell expansion count, dynamic asset and resource assignments are tested and throughput time for one or more samples is calculated. The calculated throughput time is compared against the desired time and a schedule variance is derived for each scenario of assignments, configurations, operations choices. The scenario, whose average cycle time and variation is lowest of the available choices, is comparatively optimal and robust. A full factorial simulation-optimization-sorting and ranking may be made in one embodiment on one or more CPUs and in another embodiment; a goal seeking stochastic optimization may be utilized and in another embodiment, a pruning or scenario rationalization is made.

The analytical process for dynamic control of the system's time and physical state begins with the identification of feasible resources to apply to the cell attainment, transport and expansion processes. The probabilistic task durations within those processes are derived from the simulation in an embodiment and by statistical regression in another embodiment. These durations are then consumed by the precedence based logic of the constraints based algorithm and the critical path is calculated for each scenario and its replications. Scenario and replication results are then ranked and then sorted by variation from an objective to derive the best set of control points with respect to outcome and risk. The risk (variation from objective or absolute value of deviation) may be for one quality metric or be normalized and totaled for a plurality of quality metrics.

A therapy appointment is then scheduled (step 134) according to the set of assignments and control decision set points that most robustly achieve the one or more quality metrics. This plan informs hospital operations management systems and sets the assignments for cell expansion machine capacity ahead of the actual patient cell growth activity. Once the cell expansion activity is begun, states of machines and cell growth are measured and the machine assignments and logistical controls are updated with respect to that actual rate of growth. Those corrections made to the operating controls of machines and resource assignments to attain the desired state are enabled by the system simulator with the simulation of the potential paths forward with actual state information re-initializing the model. A best new machine control point, resource or patient schedule is calculated and the analytical control system then recalculates in the next time increment so as to seek a more optimal control of system states as measured and compared to the desired state.

Figure 5:
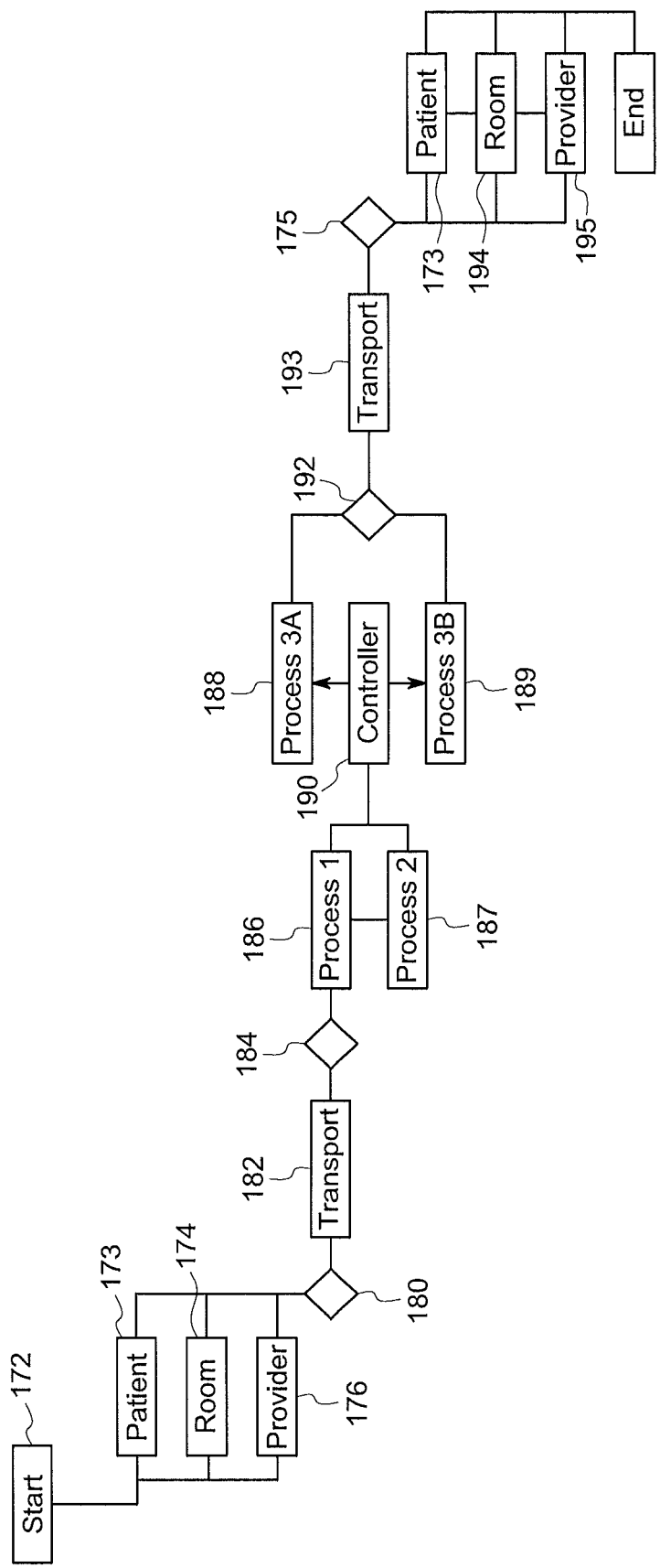
FIG. 5 is an example of a vein-to-vein cell therapy process that may be modeled for production asset utilization

FIG. 5 is an example of a vein-to-vein process that may be modeled for production asset utilization. The process begins at a start 172 point triggering a sequence of events corresponding to a cell sample acquisition which requires, in the exemplary embodiment, the concurrent presence of the patient 173, room 174 and healthcare provider 176 which each must have specific availability for the period of time required to prepare and attain the sample 180. If any one of the three requisite people or assets is not available when the tasks are scheduled, the critical path time to take the sample increases, delaying the sample's acquisition. The scheduled availability and task duration are characterized probabilistically.

Upon attainment of the patient's cell sample 180, the cells are transported 182 to arrive 184 at the cell expansion process 186. Cell quality, for example, may be defined by the target cell concentration or number of viable cells and depending on cell sample handling can degrade through time. Should the cells be attained but then delayed in transport 182 or upon arrival are delayed in processing, the cells are not being improved and in fact may be degrading. Thus there is value in controlling the processing such that upon arrival, cells are processed with minimal delay on specific machines which have been sequenced so as to be available resources in the right physical and chemical state to begin cell expansion. Likewise, should it be the case that transport 182 will be delayed, such as for predictable logistical reasons (for example—traffic, transportation resource availability, weather), the cell sample acquisition time is controlled to account for those delays, such as, taking the sample draw at a later time.

Upon cell processing 186 beginning, multiple sequences of machines, machine settings and protocols are dynamically controlled to achieve processing throughput, machine state and cell expansion rates, by the disclosed invention so as to minimize production time, maximize cell quality and, as required, produce cells using the production resources for more than one patient, optimally allocating assets to concurrently achieve these aims. An example cell expansion process may have two parallel steps 186 and 187 which, when completed, may proceed to either or both two other processes 3A and 3B, 188, 189 as routed and dynamically assigned by a controller 190 to be processed until completion. The control of process and machine assignment is orchestrated by the system controller (e.g., controller 60, see FIG. 2), which tracks all cell expansion activities and resources in the production environment. In the present example, a decision point routes and prepares two sample processing devices associated with the processes 3A and 3B. The system simulator both allows the local routing controller 190 to locally optimize the routing, such as would occur if processes 3A and B were of the same duration and quality yet one were occupied and thus the local routing decision would be to assign the other machine or process sequence. Globally however, sequencing between machines may produce a superior total facility throughput or clinical merit outcome. An example would be if process steps 3A and B orchestrated on different machines and were differentially more effective on certain cell types or cell therapy products or had different processing capabilities or limitations that interacted with various cell types or therapeutic products. The system simulator and optimizer in simulating potential paths and interactions with machines and priorities and expansion rates or quality, directs a sample to a given path (186, 187, 188, 189) in a set of simulation scenarios that improved global results. The assignment control may also be to manage to a certain time of completion from an original plan in response to one or more patient's medical state change. Other interdependent resources are thus rescheduled and routed. The delivery time of the cell therapy product 192 generated by the production may also be dynamically moved, controlling for the anticipated cell quality changes of the one or more patients and back propagated to the process control assignments.

Cell delivery time is a function of transport 193 of the processed cell therapy product 192 duration and processing time which may be changed because of a control signal or resulting from a processing rate change variation or machine or resource failure. The expansion process may be dynamically altered or the patient cell delivery rescheduled for completion at a given time(s) for the one or more patients. Administration of the cell therapy product 192 into the patient 173 (or, in other embodiments, a different patient in a non-autologous example) involves scheduling a room 194 and provider 195 qualified for administration of the cell therapy product 192.

Figure 6:
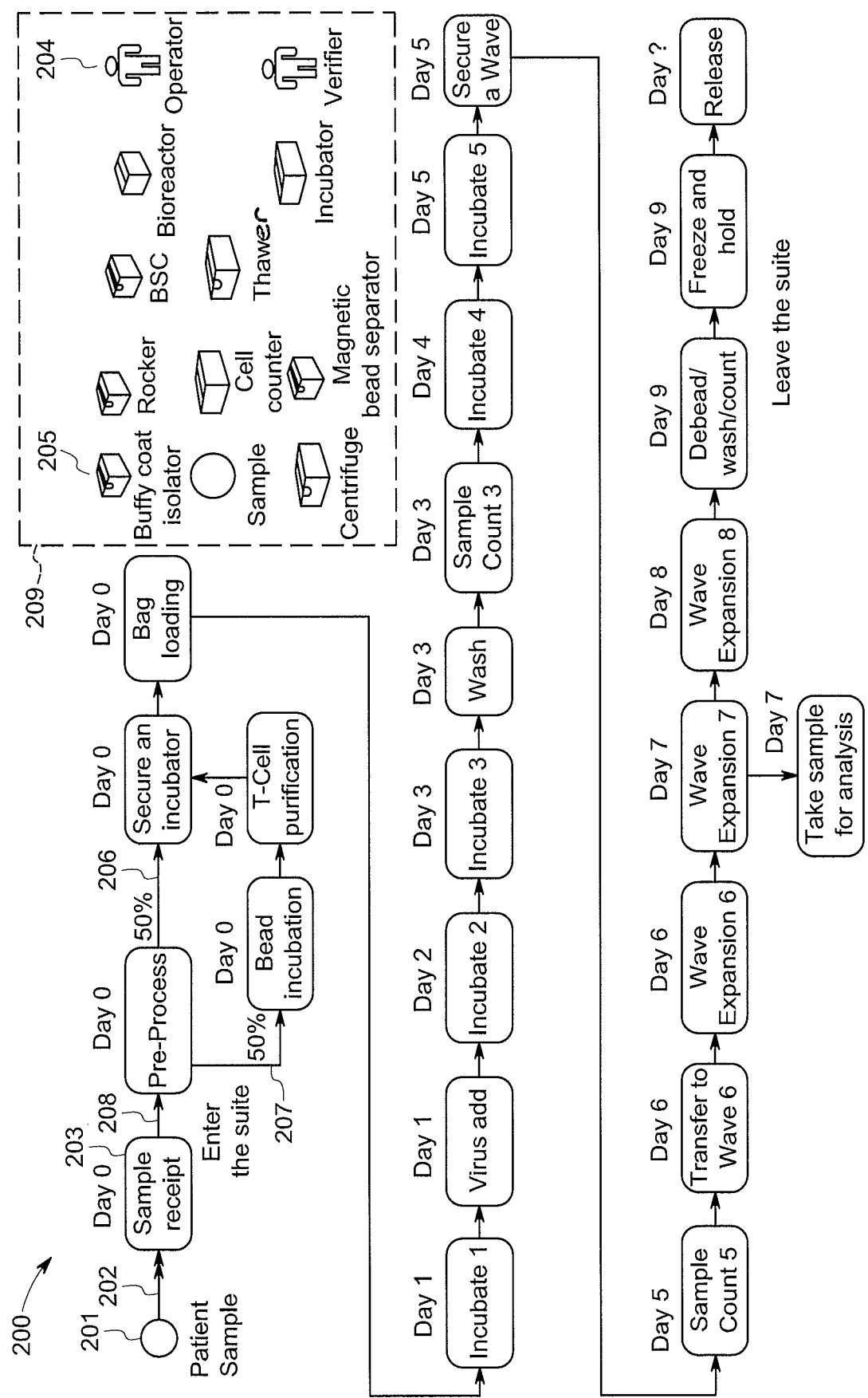
FIG. 6 is a schematic representation of a cell therapy manufacturing process according to an embodiment of the present disclosure.

FIG. 6 is a schematic representation of a workflow 200 for a patient sample 201, e.g., a blood sample provided by the cancer patient, processed through specific sample processing devices. The patient sample or samples 201 may arrive to the system at certain rate that is a function of the volume estimates or a pre-defined schedule. The arrivals can also occur randomly in terms of the quantity of the arrivals and/or the timing of the arrivals. If the arrival rate is faster than the rate of processing these entities, the total time spent in the system gets longer.

Samples 201 are processed through the workflow 200 in a certain order according to their arrival pattern 202 or as directed by the controller 60 (FIG. 2). At each process step, a sample 201 may wait in a queue before being processed until the resources are ready to process this entity. The workflow may include probabilistic routings as shown by 206 and 207.

At each process step, there may be multiple sub-steps 209 each requiring different resource(s) 204, 205 and taking different times. The resources 205 may include various devices, including a buffy coat isolator, a rocker, a biological safety cabinet (BSC), a bioreactor, a sample, a cell counter, a thawer, a centrifuge, a magnetic bead separator, and/or an incubator, presented as a non-limiting example. In the exemplar 209, the amount of time an entity spends at a process step is affected by the availability of the specific resource(s) and the amount of time for utilizing these resources. For example, if the operator (204) is not available but the incubator is available in 209, the sample 201 has to wait until both resources are available. In one embodiment, the availability of the resources 204, 205 are affected by the number of resources assigned to the overall process, their working conditions such as working hours and/or unavailability due to breakdowns or repair, and the demand for these resources by other entities in the system going through different process steps at the time the request is made. In addition, as provided herein, the workflow may include steps that provide information about the sample as it is being processed. For example, the steps may include a cell count.

Figure 7:
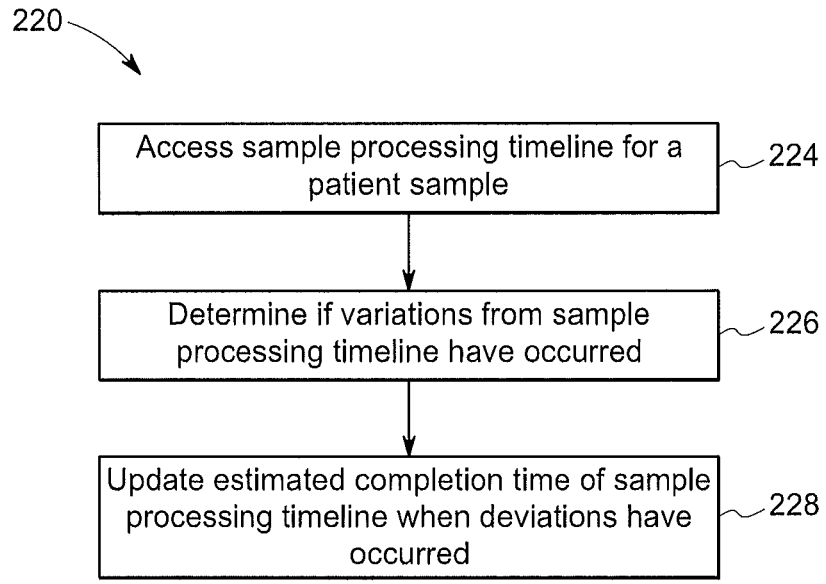
FIG. 7 is a flow diagram of a cell therapy process dynamic scheduling system according to an embodiment of the present disclosure.

The sample's progress through the workflow 200 can be affected by the variation in the arrival rates, processing rates, resource availability the processing times and the current state of the system. These interdependencies and the variation results in additional wait times. The discrete-event simulation approach captures these complexities. For example, as shown in the flow diagram of FIG. 7, a method 220 as provided herein may include the step of accessing a sample processing timeline for a particular patient sample (step 224). The sample processing timeline may be based on a production plan established at or before arrival of the sample to the cell processing facility. The sample processing timeline, as provided herein, may be an estimate or forecast model of a completion time for the sample based on empirical or historical estimates for a particular production plan. The sample processing timeline may be determined via the system 50, e.g., using simulation logic 75, resident on one or more controllers (e.g., controller 54, controller 60). The forecast may also take into account estimated resource availability for the scheduled sample based on concurrent production of other samples in the facility. When the sample is determined to vary from the timeline (step 226), which may be determined from real-time tracking of the sample, the processing step and the operator resource in the production process as well as global tracking of other samples and their committed resources, the method 220 updates the estimated completion time for the same (step 228). In this manner, the estimated completion time is dynamic to permit more accurate scheduling of patient therapy. It should be understood that certain changes in a production process may be timeline-neutral and, therefore, may not result in any updating of an estimated completion time. For example, a sample may be redirected to a different sample processing device than one originally designated on the production plan for the sample. However, such a change may not affect the timeline.

The processing protocol and/or timeline variations may include an earlier or later estimated completion time, a change in sequence of one or more steps, a change in duration of one or more steps, an addition of one or more steps, a removal of one or more steps, a change in device assignment, or a change in estimated intake date. The variations, in certain embodiments, may be triggered by events that relate to other patient samples. For example, a lack of availability of a certain device may have downstream effects for other samples. In another embodiment, the variations may be triggered by characteristics of the sample itself, such as cell count, viability, presence of biomarkers, etc. For example, a cell count below a threshold may be associated with a variation in the timeline to allow for a longer expansion cycle. A cell count above a threshold may result in a variation in the timeline to allow for a shorter expansion cycle. In one embodiment, a cell count above a threshold permits early withdrawal from an associated processing step. However, such withdrawal may be dependent on downstream device availability. Accordingly, the decision to withdraw a sample or complete a processing step early and proceed to the next step may not be implemented if the simulation logic does not determine that potential processing protocol changes will result in improved sample quality and/or a faster completion time.

Figure 8:
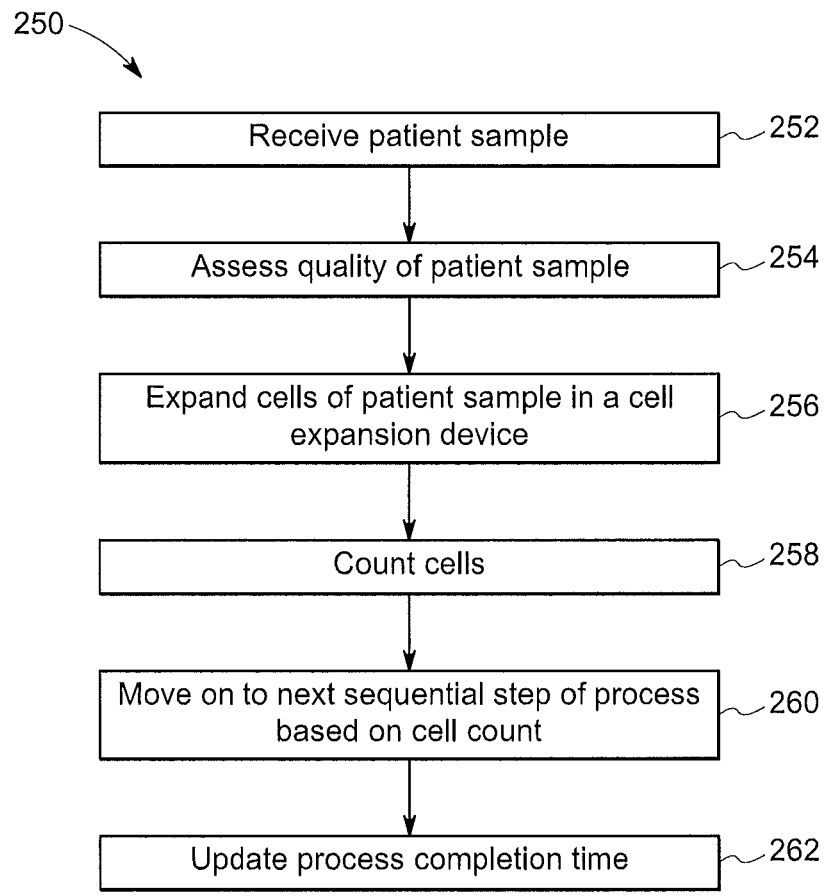
FIG. 8 is a flow diagram of a cell therapy process tracking method according to an embodiment of the present disclosure.

In another embodiment, as shown in the flow diagram of FIG. 8, the timeline may be updated based on real-time data characterizing the sample that is generated in the process. The sample is received (step 252) by the cell processing facility and placed into the process flow. In certain embodiments, sample quality may be assessed (254) when the sample is received to determine a degree, if any, of sample degradation during transport from the sample acquisition site. Based on the assessment of cell quality, the estimated process completion time may be updated. For example, the system may access data representative of average total process time for samples having similar quality attributes (e.g., cell count, cell viability, sample volume) to update the estimated process completion time, if different. In one embodiment, a low cell count or viability may be associated with a longer overall process because of increased incubation or expansion times.

During the production process, the patient sample may be processed by a series of sample processing devices. In one embodiment, the cells may be expanded in a cell expansion device (step 256) and the cells in the resultant processed sample may be counted (step 258). The cell count data may be provided to the system as an input to simulation logic to estimate a process completion time and as part of a decision to move the sample to the next sequential step of the process (step 260). For example, if the cell count is below a threshold, the sample continues with the expansion, which may result in an overall longer process and later completion time than expected. i.e., the expansion (step 256) is continued and another cell count (step 258) is performed after the expansion. These steps may be repeated until the desired cell count is reached. If the cell count is above a threshold, the sample may move to the next step, which may result in an expected-length or shorter process and an unchanged or earlier completion time. Based on the results of the cell count, the system (e.g., the system 50, see FIG. 2) may update the estimated completion time for the patient sample (step 262).

The integrated approach for designing, operating and controlling vein-to-vein cell therapy throughput systems leverages the principles of the Theory of Constraints (TOC) as the fundamental "physics" that drive the rate at which complex throughput systems generate consistent revenue through sales of products. According to TOC, there is a system constraint or a control point that limits the throughput. Usually, this control point is the process step or an area that has the longest cycle time. This is analogous to a chain connected with the multiple links. The "weakest link" on the chain defines the strength of the overall chain. Increasing the strength of the weakest link does not necessarily increase the overall strength of the chain. Alternatively, making the weakest link stronger (i.e. making the slowest process faster) will increase the overall strength of the chain (i.e. will increase the throughput of the system) which may make another link the next bottleneck (i.e. the next slowest process becomes the new bottleneck or constraint).

Figure 9:
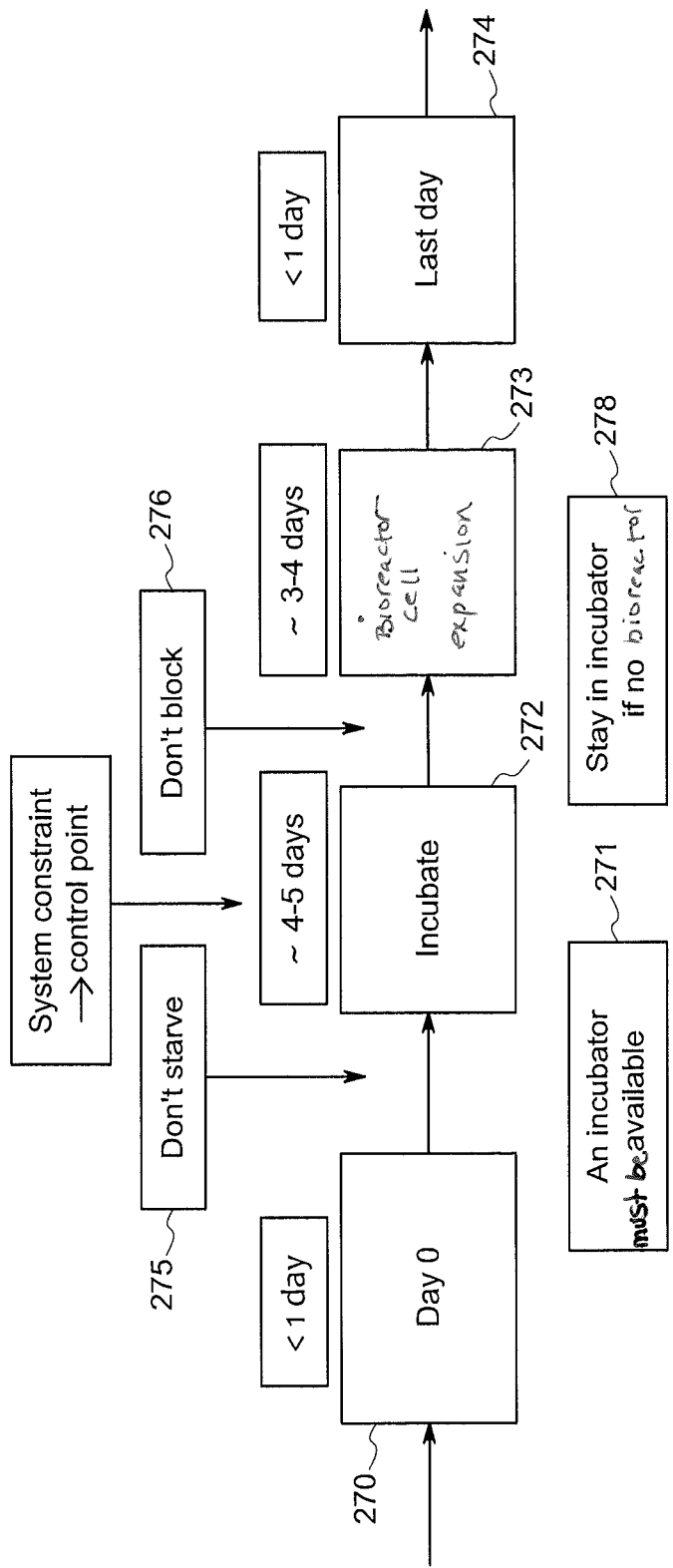
FIG. 9 is a schematic representation of a high level cell therapy manufacturing process according to an embodiment of the present disclosure.

As an example, if we consider a high level cell therapy process illustrated in FIG. 9, the incubate step 272 is the slowest step in the chain of process steps defined by 270, 272, 273, and 274. Since the system throughput is defined by this step, it is important to assure that the incubation resources are utilized at the highest level. Any leak in the capacity of the incubation resources will reduce the system throughput or revenue.

According to TOC principles, therefore, the process and operations should be designed in a way that incubation resources never starve 275 the incubator 272 to avoid being idle/not utilize the valuable resource fully. It is also key design and operational strategy to avoid blocking 276 the incubation resources caused by not having sufficient space or resources in the subsequent process step 273. For example, if a patient sample completes the use of an incubator and now has to move to a bioreactor, and if no bioreactor is available, then it may have to continue to occupy a valuable incubator space 278 when it is no longer needed. If there is another sample coming from 270 and is ready for incubation and if there is no other incubator available, the incubator resource capacity will be wasted thus reducing the revenue opportunity. TOC is also the driver for operational efficiency for predicting bottlenecks based on the current conditions. In cell therapy manufacturing, patient samples arrive in the facility as new, ready to be enhanced by the cell expansion system. When the fresh sample arrives, it needs to be prepared 270 and immediately put into an incubator 271. If an incubator is not available, other measures must be taken which may impact the quality of the patient sample, which in return may impact the efficacy of the treatment. Therefore, in one embodiment, a "just-in-time" logistics system is facilitated by controlling the patient and the hospital for the best time to obtain the sample, based on the predictive incubator space availability.

Figure 10:
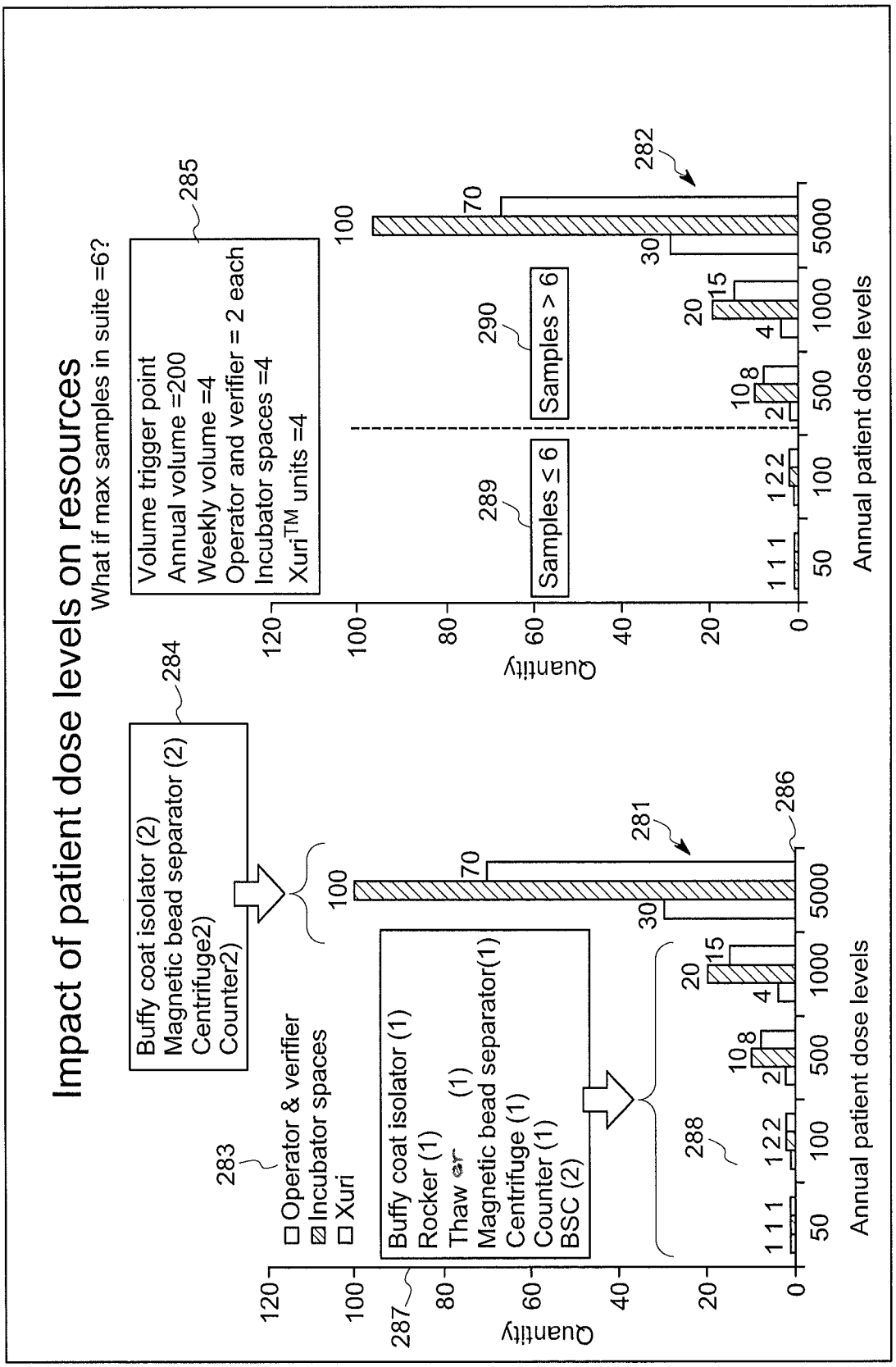
FIG. 10 is a modelling analysis of patient dose levels on resources according to an embodiment of the present disclosure.

A discrete-event simulation approach may be used for capacity planning to determine resource levels and layout implications based on the system dynamics and regulatory requirements. FIG. 10 is an example of simulation based scenario analysis.

In plot 281, the results are displayed from a set of simulation experiments conducted to determine the key resource 283 and quantities 287 based on different annual patient dose levels 286. Based on the analysis the resource levels change in order to achieve annual volume targets without unnecessary delays due to insufficient resource levels 288 and 284. This analysis may inform the decision makers, such as a manufacturing team, on the layout and space requirements based on the equipment and people levels. For example, it may be possible to achieve an annual sample unit throughput of 1000 units/yr by utilizing a single clean room. However, if the goal is to achieve a 5000 unit production level, then the same clean room will need to be replicated five times. In the plot 281, it was assumed that there is no regulatory limitation on the maximum number of open samples in the clean room. In the plot 282, similar simulation experiments were conducted with an added constraint for limiting the number of open samples to a maximum of six 289, 290. Based on this regulatory constraint and for the given assumptions in the model, the maximum volume a clean room can handle is 200 with resource levels estimated in 285. This result may have significant impact on the number of clean rooms and resource requirements within a facility.

Certain embodiments of the disclosure facilitate tracking of patient samples as they are processed to generate a cell therapy product. For example, the sample tracking information may be used as an input to simulation logic that estimates a process completion time, determines production plans based on resource availability, etc. For example, patient samples throughout a processing facility may be tracked to particular processing devices. Such devices may be indicated as unavailable based on receipt of the tracking information. That is, by associating particular samples with particular resources, a cell processing facility may assess overall resource availability. Further, the tracking information may allow the system to track sample location throughout the facility.

Figure 11:
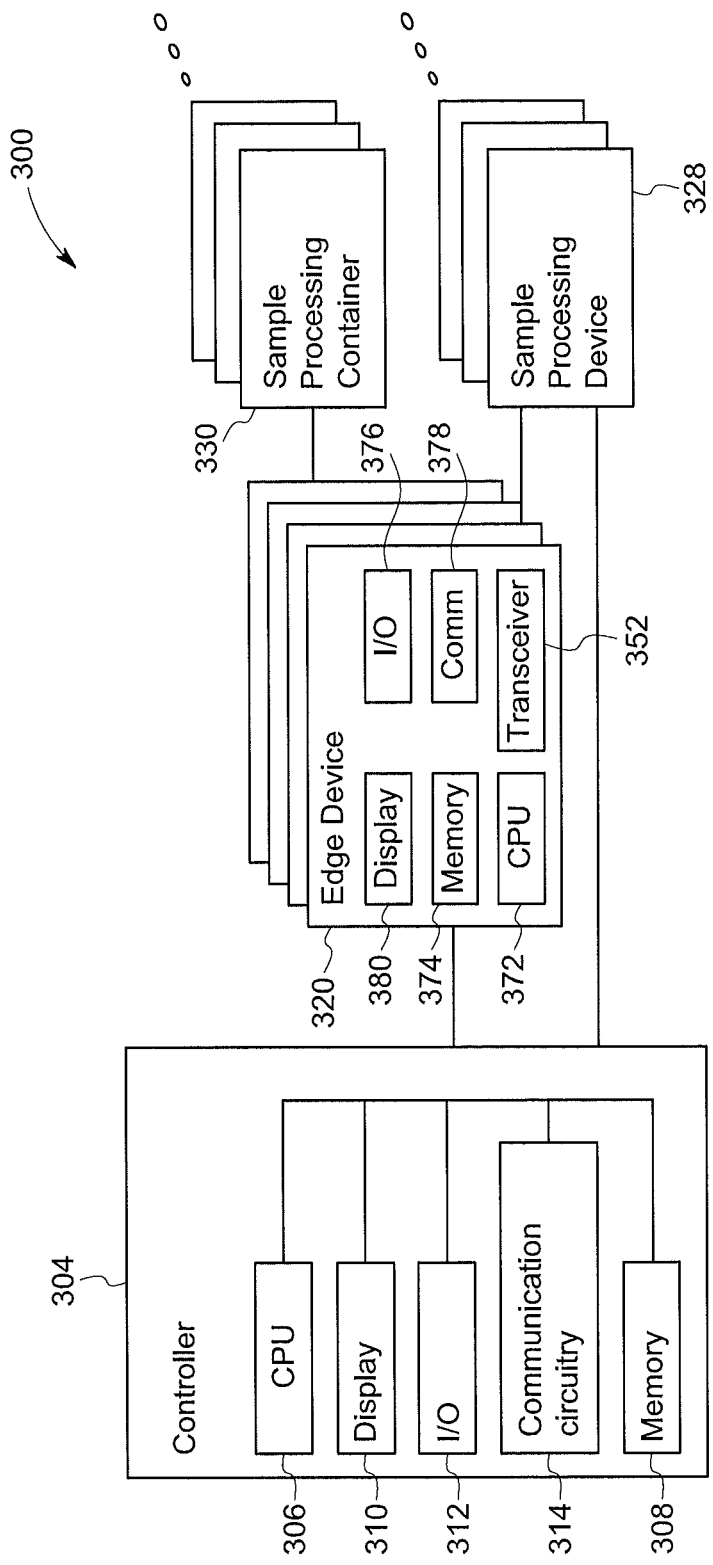
FIG. 11 is a block diagram of a cell therapy process tracking control system according to an embodiment of the present disclosure.

In certain embodiments, the disclosed techniques use a control system 300, implemented as a controller 304 as shown in the block diagram of FIG. 11. The controller may be part of a hospital scheduling controller 54 or a cell processing facility controller 60 (see FIG. 2). In the depicted embodiment, the controller 304 is implemented as a cell processing facility controller 60 that communicates with devices 328 and other components of a cell processing facility. However, it should be understood that this is merely an example, and the hardware components of the controller 304 may also be present in or implemented as the controller 54. Further, certain embodiment, the controller 304 may be implemented on one or more sample processing devices.

The controller 304 may include a processor 306, which may include one or more processing devices and a memory 308 storing instructions executable by the processor 306. The memory 308 may include one or more tangible, non-transitory, machine-readable media. By way of example, such machine-readable media can include RAM, ROM, EPROM, EEPROM, CD-ROM, or other optical disk storage, magnetic disk storage or other magnetic storage devices, or any other medium which can be used to carry or store desired program code in the form of machine-executable instructions or data structures and which can be accessed by the processor 306 or by any programmed general purpose or special purpose computer or other machine with a processor. The controller 304 may also include communications circuitry 314 and/or input and output circuitry 312 to facilitate communication with other components of the system 300. Further, the controller 304 may include a display 310 that provides a graphical user interface for operator interaction.

A reader 320 is configured to read information via receiver or transceiver hardware 352. The reader 320 may be co-located with the sample processing device 328 and any sample within a sample processing container 330 that is being operated on by the sample processing device 328. Alternatively or additionally, the reader may be co-located with a sample processing station or work space that does not include a sample processing device 328. A central processing unit 372 of the reader 320 may execute instructions stored in a memory 374. Further, the reader 320, in certain embodiments, may be implemented as an edge device. For example, when implemented as an edge device, the reader 320 may provide an entry point into a network and may include hardware circuitry such as routers, routing switches, integrated access devices (IADs), multiplexers, and a variety of metropolitan area network (MAN) and wide area network (WAN) access devices. The reader 320 may include onboard input/output circuitry 376, communications circuitry 378, and a display 380 that provides a graphical user interface for operator interaction. The reader 320 may execute routines to translate received signals that are in a particular protocol, such as an RFID protocol, into an http protocol prior to transmission to the controller 304.

The system 300, in the illustrated embodiment, includes one or more readers 320 that read identification information from and that in turn pass the identification information to the controller 304. In addition, the reader 320 may read information from a co-located sample processing device 328, which may be an incubation device, a culture device, a purification device, a separation device, a storage device, etc. The information may include device identification and parameters, such as operating parameters, as well as device location within the manufacturing facility. The identification signal may be associated with a unique patient sample in the controller, and may reference identification information such as a patient or sample number or other information to associate the sample processing container, and the enclosed sample, with a particular patient. For example, the identification signal may include a unique identifier that is associated with the patient/sample information (and, for example, the processing protocol associated with or assigned to the patient) in a database of the controller. In such embodiments, the identification signal associates the identifier with the appropriate information stored in a memory of the controller 304.

In another embodiment, an individual reader 320 co-located with the sample processing device 328 may provide the sample processing device information without reading it from the sample processing device 328 each time the device is used. That is, because the sample processing device 328 may remain the same even as the patient and/or operator changes, the sample processing device information may be stored in a memory of the device 328 and/or reader 320 for transmission to the controller 304 along with operator or patient sample information. While in the depicted embodiment, the controller 304 is implemented as a separate device from the reader 320 and the sample processing device 328, it should be understood that certain functionalities of the controller 304 may be incorporated additionally or alternatively into the sample processing device 328 and/or the reader 320. For example, the sample processing device 328 and/or the reader 320 may include a processor, memory, I/O interface, display, communications circuitry, etc. The reader 320 may also read information from one or more sample processing containers 330.

Sample information, such as data about the sample, as determined via appropriate monitoring or sensing circuitry from the sample processing device 328, may also be provided to the controller 304, either via a networked connection or through the reader 320. For example, when a sample is scheduled for a counting step, the device 328 may count the cells in the sample and the device 328 may store the cell count value or related information in an onboard memory of the sample processing device 328. The value or information may be provided to the controller 304, along with the identification information for the sample, to be used in the simulation logic for determining if the processing protocol has experienced any variations. In one embodiment, the value or information may be bundled with information read by the reader 320. In another embodiment, the controller receives the value or information, either from the reader 320 or the device 328, and associates the value or information with a sample that is determined to be at the same location based on an identification signal read by the reader 320. While the example is discussed in the context of a cell count, it should be understood that other data that characterizes the sample being processed may be provided by the sample processing device 328.

Figure 12:
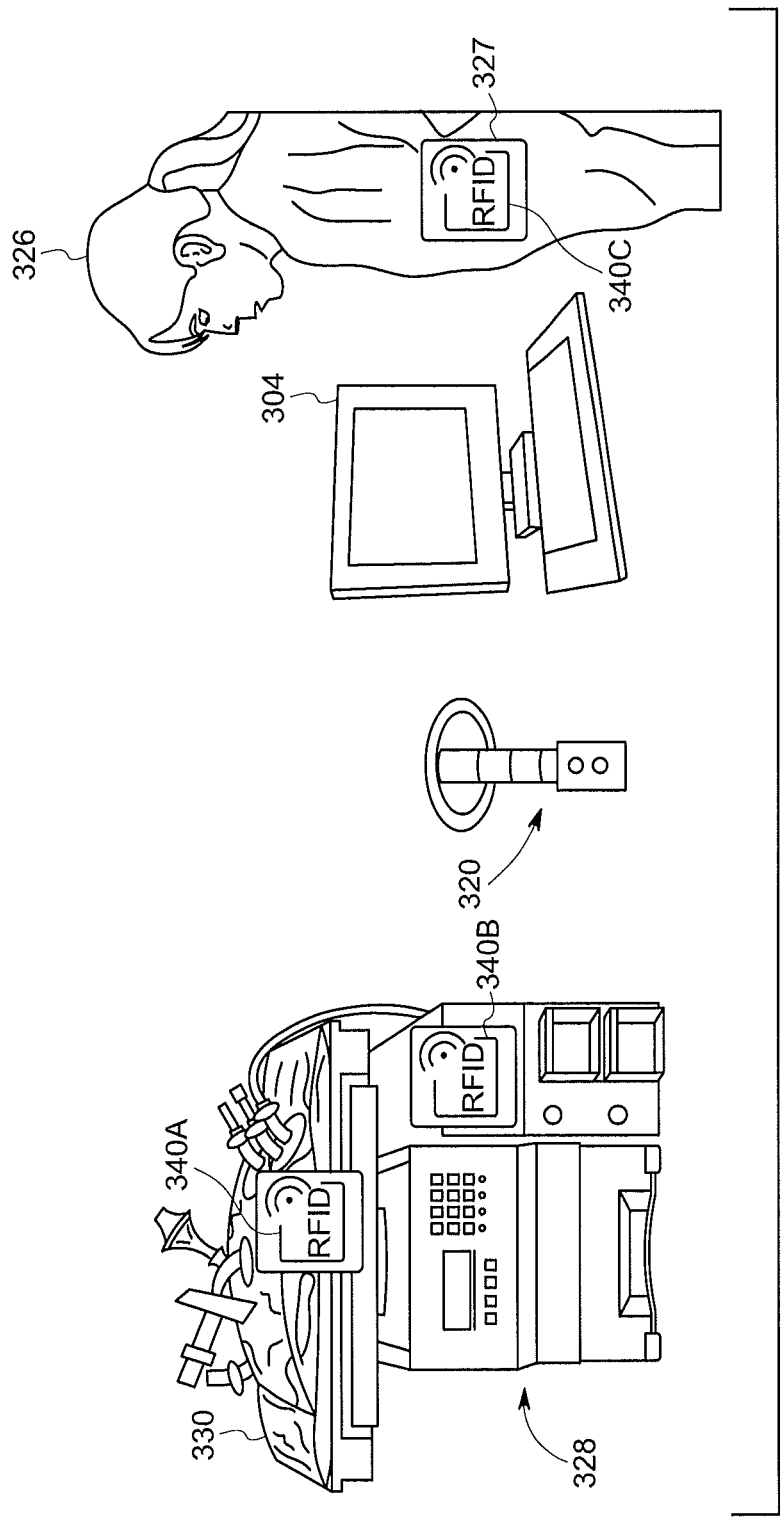
FIG. 12 is a schematic representation of an instrument control system according to an embodiment of the present disclosure.

FIG. 12 is a schematic diagram of a work station or work area within a sample processing facility. The work area represents an area for completing a step of a cell processing workflow as provided herein. One or more readers 320 read identification information associated with operators 326, e.g., via operator badges 327 and that in turn pass the identification information to the controller 304. In addition, the reader 320 may read information from a co-located sample processing device 328, which may be an incubation device, a culture device, a purification device, a separation device, a storage device, etc. During processing of a sample, the sample is transferred into the appropriate sample processing container 330 for use with the sample processing device 328. The reader 320 reads information from tracking devices 340, shown as RFID tags, e.g., a tracking device 340*a* on the sample processing container and, in certain embodiments, a tracking device 340*b* on the sample processing device. The information from the sample processing container 330 may include the patient identity of the patient sample. The information may also include identification information or specifications of the sample processing container 330. In one embodiment, the sample processing container includes its own label or tag with container identification information that may be read by the reader 320. However, such information may additionally or alternatively be provided via the tracking device 340*a*. The information from the sample processing device 328 may include device identity and/or operating parameters. The reader 320 may also capture information from a tracking device 340*c* on the operator badge 327. The information read from the tracking devices 340 by the reader 320 is sent to the controller 304 for confirmation that the workflow associated with the patient is being followed, which may be indicated via the reader 320. The controller 304 may be located within the work area and may, in certain embodiments, include its own dedicated reader 320 to prevent the operator from having to badge in within a clean room where the sample is located. In other embodiments, the controller 304 is remote from the work area. The signals from the reader 320 are provided to the controller 304 and may be used to estimate completion time for one or more samples. The reader 320 may be integrated into the sample processing device 328 in certain embodiments.

The cell production samples and production facilities preferentially employ asset management to ensure safe operation and reduce overall operation costs. Sample asset management may include a reader as provided herein and an autonomous active control and interactive tag that maintains secure handling of cell samples should the master control system fault or become disconnected.

A plurality of sample containers are often moved from one location to the next such as from different collection sites and processed by various machines, with some uncertainty arising regarding a present location of a specific container at any given time. As operators move containers from one location to another, or move groups of containers to access a specific container, the likelihood of a container being misplaced or placed onto the wrong machine or intermingled with other samples increases.

The process of reading and communicating with the tracking device generally includes bringing the tracking device in proximity to a sensor. The tracking devices can include active RFID tags operable to emit an RF signal (or alternatively pulsed beacon), or RFID tags that are passive until illuminated by the radio frequency field of the RFID sensor, at which point they transmit a signal back to the RFID sensor. In addition to radio frequency, other types of tracking technology communication mediums can include optical (e.g., frequency, pattern or intensity of light), infrared, electromagnetic, ultrasound, etc. or combinations thereof.

Certain tracking technology exhibits low durability and often requires substantial replacement costs. For example the tracking technology is comparatively high cost with its active communication, local processing and interactive display. With reuse, there is an increased likelihood of failure associated with cleaning or disinfection. Another cause for increased likelihood of failure of the tracking technology can be associated with exposure to other samples, bacteria, dirt or other contamination. There is a need for improved durability so as to lower the likelihood of failures caused by maintenance, cleaning, disinfection, or sterilization. Further, maintenance and downtime may be scheduled during estimated gaps in resource usage.

Figure 13:
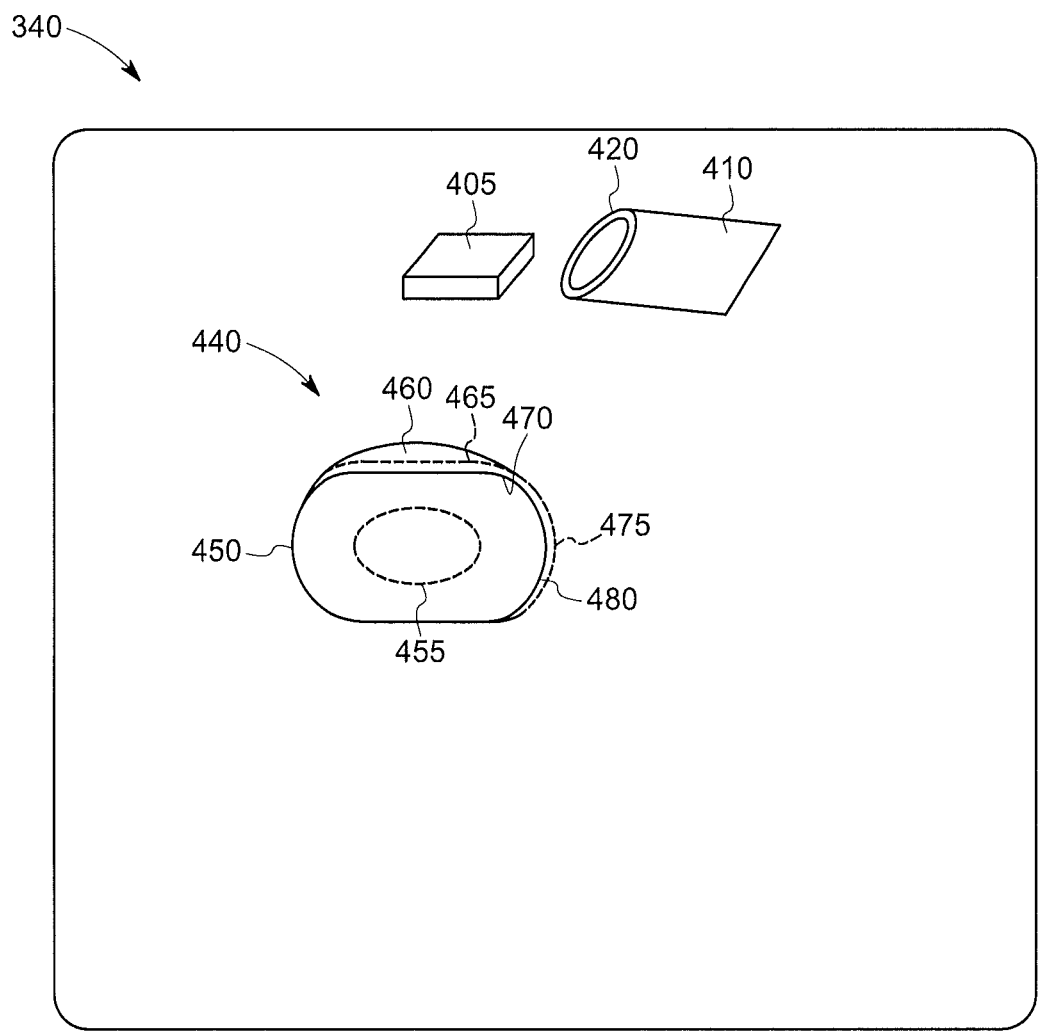
FIG. 13 is an illustration of a tracking device assembly according to an embodiment of the present disclosure.

Provided herein are tracking devices and assemblies with a protective element that protects the higher cost portions of the device to facilitate reuse. FIG. 13 illustrates an example of a tracking device 340 that includes a first encapsulate film 420 configured to receive a tag 405. The first encapsulate film 420 may be formed from a waterproof or vapor proof material (e.g., polyethylene, polystyrene, etc.). The material composition of the first encapsulate film 420 may be translucent such that a person can visualize the identification of the portable device enclosed therein and read its screen and/or interact with it via a capacitive coupling or pressure contact. The first encapsulated film 420 may be generally configured to completely enclose the device and prevent penetration and/or be impervious to fluids and dirt. The first encapsulate film 420 may be configured to isolate the tracking tag from exposure to sustained mechanical and fluid immersion contact and prevent penetration of antiseptics, disinfectants, and soaps. The first encapsulate film 420 may also be configured to isolate the tracking tag from exposure to or prevent penetration of plasma gases, ultraviolet light, or radiation exposure.

The material composition of the first encapsulate film 420 may be translucent to various tracking technology mediums (e.g., optical recognition, bar code, radio frequency, infrared, ultraviolet light, etc.) to allow the tag 405 to communicate with a remote tracking station (e.g., transmitter, receiver or transceiver or combination thereof) of the tracking system.

An embodiment of the first encapsulate film 420 may be operable to shrink or reduce in size in response to a threshold application of energy (e.g., threshold heat from an application of a stream of hot air blown from a hairdryer, threshold frequency or intensity of light) such that the film can seal the portable device therein from exposure to fluids (e.g., water, vapors, air). The encapsulation of the first encapsulate film 420 may be enclosed such that dirt or bacteria cannot penetrate through to reach the tracking tag 405 worn on the object 410. An embodiment of the encapsulate film 420 may be applied with various embodiments, including: shrink wrapping with hermetic fusion sealing, wrapping and enclosed with glue, or mechanical interference sealing. The first encapsulate film 420 may include one or more layers.

An embodiment of the encapsulate film 420 can include a visual indicator or electronically-formatted status indicator stored and retrievable from a non-transitory storage medium representative of a remaining time period of a disinfection status of the tracking device. An embodiment of the encapsulate film 420 can include, solely or in combination with the above, a visual indicator or electronically-formatted status indicator stored and retrievable representative of a current measure of chemical penetration of any disinfection solvents that have been in contact or penetrated the encapsulation film 420 or made contact with the tag 405 enclosed within. In one embodiment, a small display, such as for example a liquid crystal driven via a local processor that computes models and alerts provides measures, alarms, state information and optical codes that are then made to be viewable through the encapsulating film.

The tracking device 340 (FIG. 13) can further include a bag with a band or attachment 440 configured to receive the first encapsulate film 420 and the tag 405 enclosed therein. The band 440 may be configured to receive or mechanically fasten to an appendage of the bag or container of object 410 so as to support the location tracking and tag 405. One embodiment of the band 440 can include a tubular form constructed of material composition operable to encircle or receive the appendage of the object 410.

The material construction of the band 440 can further include a sleeve having a receptacle for receiving the tracking device 340, such as a pouch or pocket portion 450 configured with a flap portion 455. The pocket portion 450 can include an open end 460 to a defined space of the pocket portion 450 generally configured to receive the first encapsulated film 420 and tracking tag 405 enclosed therein. The pocket portion 450 may be integrally constructed with or attached by mechanical connection device (e.g., Velcro, adhesive, snap connector, etc.) or thermal fusion or chemical bond to the band 440. The flap portion 455 may be integrally constructed to or connected by a mechanical connection device (e.g., Velcro, adhesive, snap connector, etc.) or thermal fusion or chemical bond to the pocket portion 450. The flap portion 455 may be generally configured to overlap the open end 460 so as to restrain the tracking tag 405 within the pocket portion 450 of the band 440.

The pocket portion 450 and flap portion 455 of the band 440 may be comprised of a material composition that reduces in size or shrinks in response to receiving an application of a threshold energy (e.g., frequency or intensity of light, increased temperature from application of hot air from a hairdryer, etc.) so as to seal the pocket portion in a manner to inhibit penetration of dirt or debris or splashed fluids (e.g., blood, water) into the pocket portion 450.

The band 440 may be constructed in a similar manner to respond to an application of energy (e.g., blow of warm air from a hair dryer or similar device) so as to tighten or reduce in size around the person's appendage. Further, the material composition of the band or the pocket portion and flap portion may be generally translucent so as to allow a person to generally visualize the identification of the tracking tag 405 enclosed therein.

The embodiment of the band 440 and/or the pocket portion 450 may be integrally constructed with the film or independent thereof. The band 440 or pocket portion 450 can also be attached to the encapsulation apparatus by a mechanical connection device (e.g., adhesive, buckle, clamp, Velcro, etc.) 465. The band 440 may be comprised of a similar material composition as that of the encapsulation apparatus so as to shrink or reduce in size in a similar manner in response to a threshold application of energy (e.g., threshold frequency or wavelength or intensity of light, threshold temperature of hot air blown from a hair dryer). In another embodiment, the band 440 can include one or more straps secured around the appendage of the person by a mechanical device (e.g., adhesive, clamp, buckle, Velcro, etc.) 470.

Embodiments of the tracking tag 405 can include an antenna, receiver, transmitter, or transceiver or combination thereof configured to communicate in a known manner via a tracking technology medium (e.g., optical recognition, bar code, radio frequency, infrared, ultraviolet light, etc.). The tag 405 may be employed in combination with stationary sensors to track locations of objects and other desired parameters of the object relative to a predetermined landmark or area. The tag 405 may be a passive tag that in response to receiving a first signal from a fixed tracking system then transmits a signal with an identifier of the person or asset wearing the tag. The tag 405 can also be an active tag that transmits a signal with an identifier of the sample on a continual or periodic basis.

The tag 405 contained in the first encapsulation film 420 and/or the band 440 may include an energy source 475 to power the tag 405, the types of energy sources 475 including a battery, an energy harvesting technology operable to convert motion, vibration, solar energy, thermal energy, radio-frequency energy, etc. to electrical energy to power the tracking tag and/or other sensors employed in combination therewith. In one embodiment, the tag 405 may be powered by the sample processing device in use. For example, when the device is a rocker, the rocking motion may power the tag 405. In this manner, when the device is not operational, no power is provided to the tag 405. In turn, no tracking information for the sample is received. The first encapsulation film 420 and/or the band 440 may be further configured to receive paper or other printable medium so as to be printed with an identification code or name of the object wearing the tracking device 340. The band 440 may be marked with a color patterns or combination thereof to provide visual identification. The band 440 may be marked so as register with an optical scanner (not shown). The band 440 may have its color patters dynamically changed by an internal or external triggering device to indicate a change in state. The band 440 and first encapsulation film 420 may include at least a defined window space 480 translucent so as to transmit a passive RFID or infrared signal or optical signal that may be continuous, or triggered endogenously or exogenously. The diameter of the band 440 may be variable to be attached to various types of container or bags 410, including physical devices, disposable items. An embodiment of the band 440 can include a mechanical connection device to avoid re-expansion after shrink fitting.

The tracking device 340 may be configured to receive and protect other types of electronic devices 405 susceptible to an increased probability of failure or improper operation with exposure to disinfectants or bodily fluids or debris, such devices 405 (e.g., sensors) including those to record or measure sound, blood sugar level, saturated oxygen levels, temperature, blood pressure, light, electrical conductance, motion or vibration, RF signals, optical signals, infrared signals; devices to create electrical fields at the skin surface; devices to dispense medication (e.g., via a pump, flow control, skin absorption, etc.); devices to record ultrasound; an output device such as an LCD screen; and devices such as position tracking sensors (electromagnetic sensors); and those including electrodes to detect and store bio potential signals (e.g., pulse, electrocardiogram, etc.) generated by a human.

Having described a general construction of the embodiment of the tracking device 340, the following is a general description of a method of operation of the tracking device assembly 340 described above.

The method can include enclosing the tag 405 in the tracking device 340, such that cell, dirt and bacterial contamination generally do not penetrate through the device 340 and make contact with the tag 405. An embodiment of the tracking device 340 may be reduced in size or shrunk to wrap around the electronic device 420. Assume for sake of example that the electronic device 420 includes a tracking or tracking and control device 405. The method of enclosing the tag 405 can include immersing the tag 405 into a solvent-impermeable casing, where casing is soft or hard, so as to form the encapsulation film 420 around the device 405. The encapsulation film 420 can include the ability to incorporate straps or other mechanical connector 470. The encapsulation film 420 may be fabricated from a material composition that is chemically resistive against penetration of disinfection solvents employed to disinfect in a healthcare environment or clinic setting.

The method can further include providing the band 440 with the pocket portion 450 to receive the encapsulation film 420 and enclosed electronic device 405. The embodiment of the band 440 can include a tubular type form of plastic material composition configured to receive an appendage of the sample container or persons also being tracked and controlled. The pocket portion 450 may be integrally constructed to or attached by a mechanical connection (e.g., adhesive, Velcro, buckle, etc.) to the band 440. The flap portion 455 may be coupled to generally overlap the pocket portion 450. With insertion of the encapsulation film 420 and enclosed tag 405 in the open end 460 of the pocket portion 450, the flap portion 455 may be folded over the opening to enclose the encapsulation film 420 and tag 405 in the pocket portion 450 of the band 440. The material composition of the band 440 and attached pocket portion 450 may be generally similar to the material composition of the encapsulation film 420 such that an application of energy (e.g., heat, chemical, etc.) can cause the flap portion 455 and pocket portion 450 to generally bond so as to seal the enclosed encapsulation film 420 and tag 405 from exposure to fluids (e.g., water, vapor, disinfection chemicals, etc.) or other contamination. The material composition of the encapsulation film 420 and the pocket portion 450 of the band 440 may be such that the person can visualize the identity of the tag 405 enclosed therein. With insertion of the appendage 465 into the band 440, an application of energy as described above can cause the band 440 to reduce in size or shrink fit around the appendage 465 in a snug manner to prevent removal. A clinician or technician can visualize and store the identity of the tag 405 with the identity of the object 410 receiving the band 440 so as to be operable to track and store movement of the object 410 through treatment or diagnosis at the facility.

Upon time to end tracking of the sample and/or persons, removal of the tracking device 340 can include cutting the band 440 to release or remove from the appendage 465 or object 410. The band 440 itself may be disposed of while the encapsulation film 420 and enclosed tag 405 may be retained, disinfected and used again. Disinfection of the encapsulation film 420 and enclosed tag 405 can include cutting the pocket portion 450 of the band 440 to remove the encapsulation film 420 and enclosed tag 405, without disturbing the construction of the encapsulation film 420 around the tag 405, and applying disinfectant or other cleaning solution at the encapsulation film 420 and enclosed tag 405. Applying disinfectant or other cleaning solution can include wiping or immersion of the encapsulation film 420 and enclosed tag 405 in the disinfectant or cleaning solution. For example, the encapsulation film 420 and enclosed tag 405 may be completely immersed in the disinfectant (e.g., CIDEX™) for a threshold period of time. The encapsulation film 420 prevents the disinfectant from penetrating and making contact with the enclosed tag 405 that would otherwise increase the likelihood of corroding or otherwise damaging the tag 405 and thereby prevent subsequent re-use of the tag 405 with another person. The encapsulation film 420 and enclosed tag 405 can also be sterilized by immersion in steam vapor for a threshold time period. Reuse may also include overwriting or erasing existing identification data stored on the tag 405.

The electronic device including its display, battery and sensors may be sensitive to temperature. The present invention, in its ideal embodiment, is designed and applied as a system with an intended use-case. For example, a thermal mass situated on the inside of the encapsulation film 420 around device 405 may be designed so as to absorb thermal energy over the duration of disinfection of sterilization such that the electronic device and its associated components remain below their threshold temperature damage point by virtue of heat absorption in the thermal mass. The said thermal mass is selectable in its designed density as a function of distance from the film 420 and encapsulated device 405 so as to allow the film 420 to reach and stay at the requisite temperatures while device 405 also retains its design temperature range. After disinfection, the tag 405 enclosed in the encapsulation film 420 may be made available for use with another object 410 in a similar manner as described above.

Figure 14:
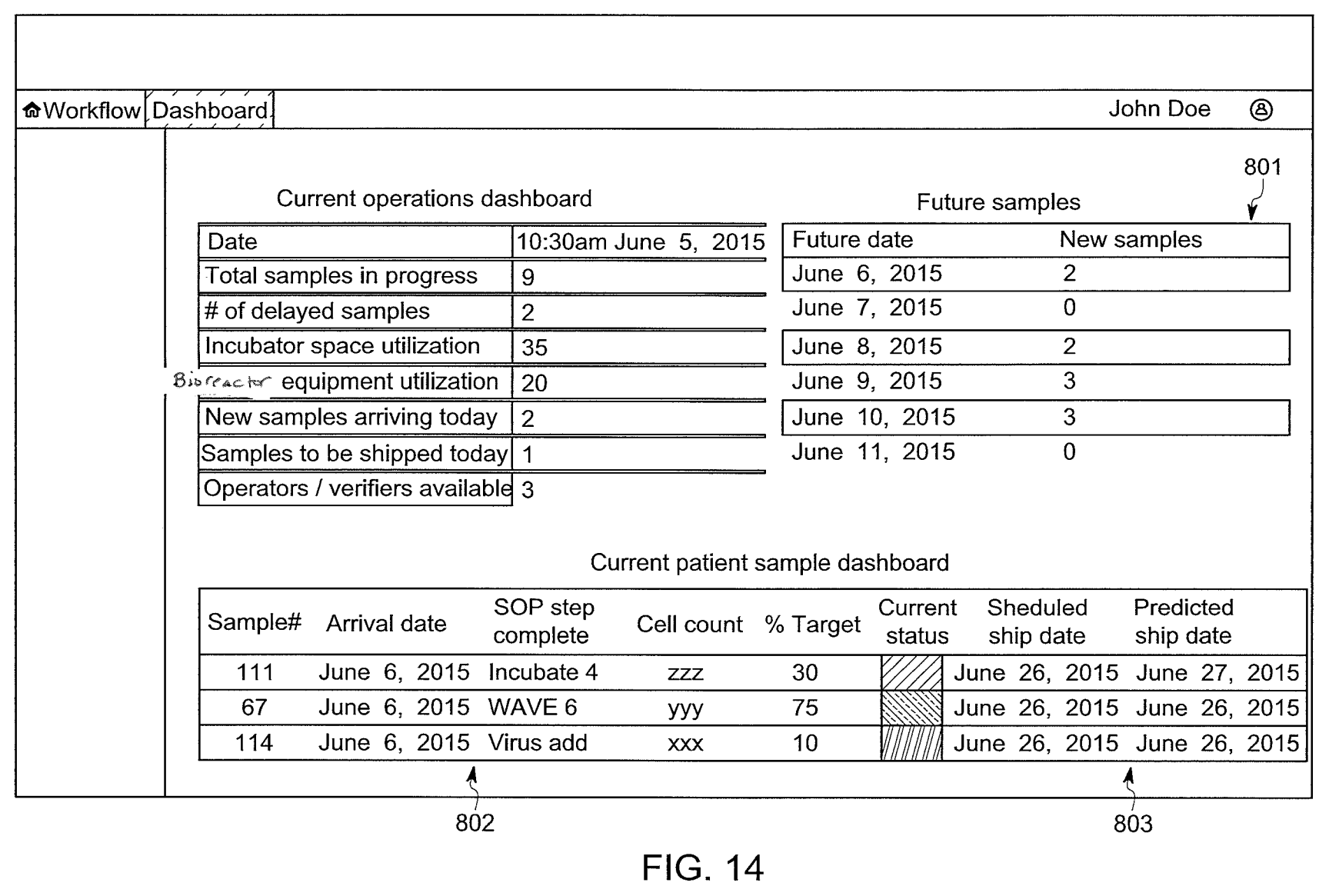
Figure 15:
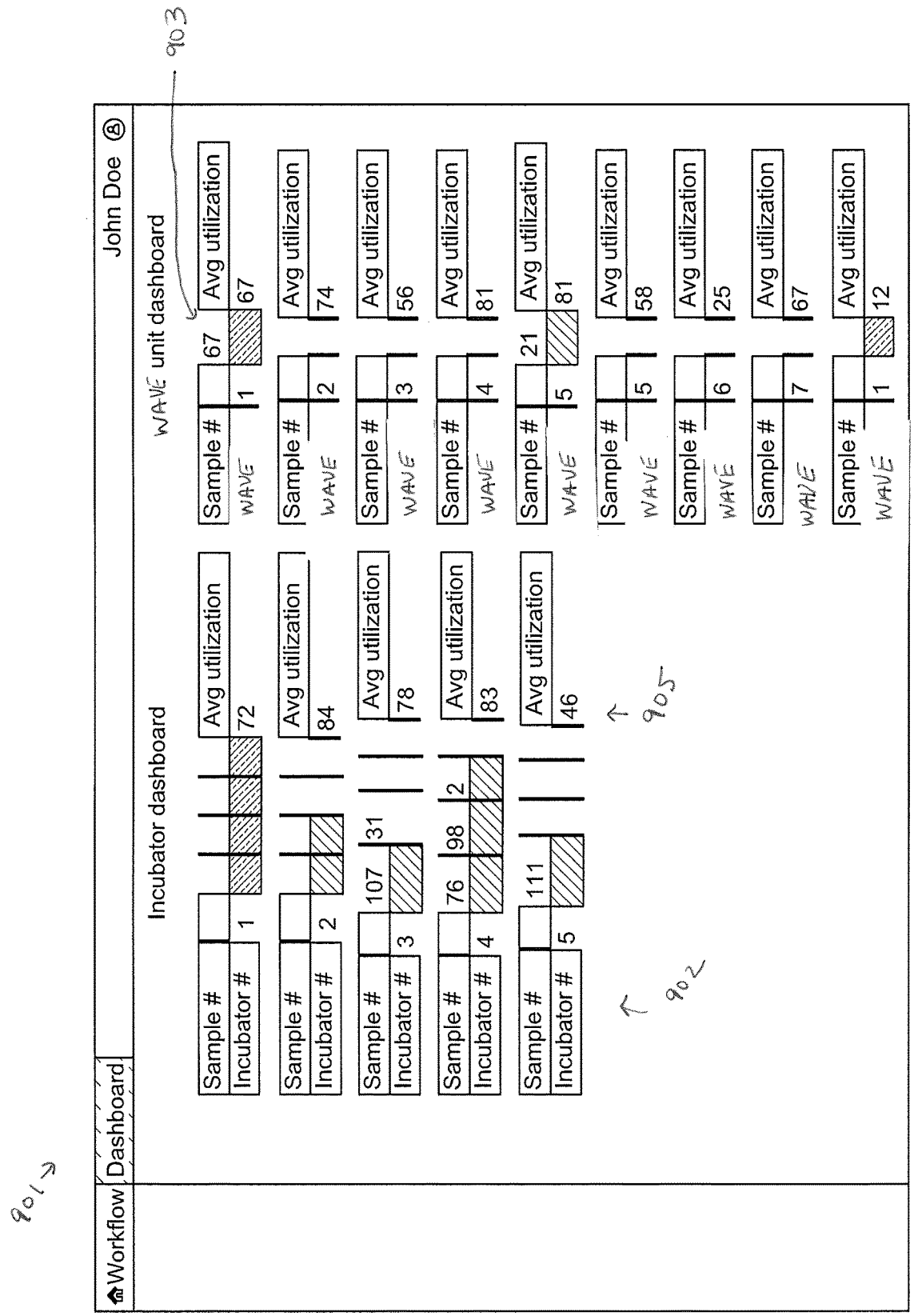
FIG. 15 is an example of a user interface for tracking availability of resources real-time in a cell therapy process according to an embodiment of the present disclosure.

The disclosed embodiments may also be used in conjunction with one or more operator interfaces. FIGS. 14 and 15 are examples user interface display that may be used to track validation of a workflow for a patient sample. The illustrated display may be used in conjunction with the system 50 (see FIG. 2) to schedule patients and track patient samples. For example, in FIG. 14, new samples 801 may be tracked and information such as the sample arrival date 802 and estimated completion times 803 may be displayed. Other display screens of the user interface may provide workflow overviews, sample tracking, real-time process updates, etc. The timing and the quantity of the future samples 801 can be determined by initializing the simulation model with the current state for samples, equipment and human resource states and availability and simulating the future state. FIG. 15 is an example of displaying the current asset utilization 901 including which samples are occupying which assets 902, 903 and the long term utilization 905 of each asset for capacity planning and preventative maintenance.

Technical effects of the invention include improved sample tracking and throughput for cell therapy production. The disclosed techniques facilitate improved utilization of cell therapy product manufacturing resources with less downtime. Further, control of the processing equipment may be dependent on adherence to prior steps in the workflow. Such techniques may be used to improve throughput and quality of cell therapy production. In addition, the disclosed techniques may improve patient scheduling and hospital and provider resource utilization for cell therapy patients.

This written description uses examples to describe certain embodiments, including the best mode, and also to enable any person skilled in the art to practice the invention, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A cell therapy manufacturing system to achieve a targeted cell count of expanded cells in a given time, comprising:
    a sample container configured to hold a cell therapy sample;
    a tracking device coupled to the sample container;
    a bioreactor configured to process the cell therapy sample;

a reader co-located with the bioreactor or a sample processing station, and configured to receive an identification signal from the tracking device; and a controller operatively coupled to the reader and configured to:

receive the identification signal from the tracking device at a time using the reader;

automatically access a sample processing timeline of a processing protocol associated with the identification signal, wherein the sample processing timeline is estimated using a discrete-event simulation providing a forecasted probabilistic duration for a cell expansion in the bioreactor to arrive at a targeted cell count of expanded cells in the cell therapy sample, during the computed processing protocol duration;

automatically determine a real-time cell count of expanded cells in the cell therapy sample using the bioreactor at the time the identification signal is received;

determine if variations from the processing protocol have occurred that alter the sample processing timeline based at least in part on the time of receipt of the identification signal and the real-time cell count;

determine one or more estimated updated completion times of the processing protocol using the discrete-event simulation by updating a set of assumptions used in the discrete-event simulation with at least the real-time cell count of expanded cells in the cell therapy sample of the bioreactor, quality state information of the cells in the cell therapy sample of the bioreactor, and availability of a next sample processing device in a workflow of the cell therapy sample; and automatically send the one or more updated completion times of the sample processing timeline to sample processing devices when the one or more updated completion times are different from a previous completion time of the sample processing timeline, wherein the updated completion times are used to allocate sample processing assignments and change flow patterns of the cell therapy sample within the sample processing devices, and wherein the flow patterns of the cell therapy sample are a function of optimal machine assignment and machine availability, reliability, or comparative effectiveness on a given cell sample.

2. The system of claim 1, wherein the one or more estimated updated completion times comprise a plurality of estimated completion times for a respective plurality of potential processing protocols and wherein the controller is configured to select one of the potential processing protocols based on a respective estimated completion time.

3. The system of claim 1, wherein the controller is configured to further determine if variations from the sample processing timeline have occurred based at least in part on an identity or location of the sample processing station and the sample container; and the duration of the sample container at each sample processing station.

4. The system of claim 1, wherein the controller is configured to provide a later updated completion time based on real-time cell count being below a threshold.

5. The system of claim 1, wherein the controller is configured to provide an earlier updated completion time based on real-time cell count being above a threshold.

6. The system of claim 1, wherein the controller is configured to estimate the one or more updated completion times to have a larger block of time for the bioreactor based on a lack of availability of the next sample processing device in the workflow of the cell therapy sample.

7. The system of claim 1, wherein the controller is configured to mark the bioreactor as unavailable for another cell therapy sample when the sample container is in a range of the receiver.

8. The system of claim 1, wherein the bioreactor accommodates a plurality of cell therapy samples simultaneously for processing and wherein the controller is configured to mark a processing slot of the bioreactor as unavailable when the sample container is in a range of the reader.

9. The system of claim 1, wherein a motion of the bioreactor is configured to power the tracking device and wherein the controller is configured to determine that the bioreactor is in operation based on receipt of the identification signal.

10. The system of claim 1, wherein the controller is configured to use the sample processing timeline and the updated completion time as input to provide an estimated completion time of a similar cell therapy sample.

11. The system of claim 10, wherein the similar cell therapy sample has a similar cell count or viability percentage as the cell therapy sample.

12. The system of claim 1, wherein the tracking device comprises an RFID tag and the reader comprises an RFID reader.

13. The system of claim 1, further comprising a sealable receptacle incorporated into or coupled to the sample container, wherein the tracking device is encapsulated by a fluid-resistant film and disposed in the sealable receptacle, and wherein the tracking device encapsulated by a fluid-resistant film is configured to be removed from the sealable receptacle by an operator to be sterilized and reused, wherein the tracking device stores identification information for the patient sample that is erased or overwritten when the tracking device is reused.

14. The system of claim 1, wherein the controller, during the communicating step, is further configured to send a decision signal to move the cell therapy sample to the next sample processing device if the real-time cell count of expanded cells in the cell therapy sample is above a threshold.

15. The system of claim 1, wherein the controller, during the communicating step, is further configured to send a decision signal to continue expansion of the cell therapy sample in the bioreactor if the real-time cell count of expanded cells in the cell therapy sample is below a threshold.

* * * * *